United States Patent
Redfield et al.

(10) Patent No.: US 11,364,242 B2
(45) Date of Patent: Jun. 21, 2022

(54) TREATMENT AGENTS FOR INHIBITING HIV AND CANCER IN HIV INFECTED PATIENTS

(71) Applicants: Robert R. Redfield, Baltimore, MD (US); Alonso Heredia, Washington, DC (US); Charles Davis, Laurel, MD (US); Ronald Gartenhaus, Pikesville, MD (US); Edward A. Sausville, Edgewater, MD (US)

(72) Inventors: Robert R. Redfield, Baltimore, MD (US); Alonso Heredia, Washington, DC (US); Charles Davis, Laurel, MD (US); Ronald Gartenhaus, Pikesville, MD (US); Edward A. Sausville, Edgewater, MD (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

(21) Appl. No.: 16/580,988

(22) Filed: Sep. 24, 2019

(65) Prior Publication Data

US 2020/0016160 A1 Jan. 16, 2020

Related U.S. Application Data

(63) Continuation of application No. 15/159,444, filed on May 19, 2016, now abandoned.

(60) Provisional application No. 62/163,408, filed on May 19, 2015.

(51) Int. Cl.
*A61K 31/519* (2006.01)
*A61K 31/44* (2006.01)
*A61K 31/4745* (2006.01)
*A61K 31/501* (2006.01)
*A61K 31/5377* (2006.01)
*A61K 45/06* (2006.01)

(52) U.S. Cl.
CPC ........ *A61K 31/519* (2013.01); *A61K 31/4745* (2013.01); *A61K 31/501* (2013.01); *A61K 31/5377* (2013.01); *A61K 45/06* (2013.01)

(58) Field of Classification Search
CPC ... A61K 31/519; A61K 31/4745; A61K 31/46
USPC ..................... 514/262.1, 292, 304
See application file for complete search history.

(56) References Cited

U.S. PATENT DOCUMENTS

| 2014/0018354 A9 | 1/2014 | Moorman et al. |
| 2014/0066474 A1 | 3/2014 | Fritsch et al. |

OTHER PUBLICATIONS

Mencarelli et al. "CCR5 antagonism by Maraviroc reduces the potential for gastric cancer cell dissemination," Translational Oncology, 2013, vol. 6, No. 5, pp. 784-793 (Year: 2013).*

(Continued)

*Primary Examiner* — Shengjun Wang
(74) *Attorney, Agent, or Firm* — Wolter Van Dyke Davis, PLLC; Eugene Molinelli; Martha Cassidy

(57) ABSTRACT

Methods are provided for treating HIV and cancer in a subject in need thereof by administering to the subject therapeutically effective amounts of an mTOR inhibitor. Other methods are provided for treating subjects infected with HIV by administering to the subject therapeutically effective amounts of the mTOR inhibitor INK128, GSK2126458, AZD2014 or Torin-2.

4 Claims, 12 Drawing Sheets

Specification includes a Sequence Listing.

(56) References Cited

OTHER PUBLICATIONS

Pirrone et al. Combination approach to prevention and treatment of HIV-1 infection, , Antimicrobial Agents and Chemotherapy, 2011, vol. 55, No. 5, pp. 1831-1842. (Year: 2011).*

Chi, Hongbo, "Regulation and Function of mTOR Signalling in T Cell Fate Decisions", "Nature Reviews Immunology", May 1, 2012, pp. 325-338, vol. 12, No. 5, Publisher: Macmillan Publishers Ltd., Published in doi:10.1038/nri3198.

Dorr, Patrick, et al., "Maraviroc (UK-427,857), a Potent, Orally Bioavailable, and Selective Small-Molecule nhibitor of Chemokine Receptor CCR5 . . . ", "Antimicrobial Agents and Chemotherapy", Nov. 1, 2005, pp. 4721-4732, vol. 49, No. 11, Published in: doi:10.1128/AAC.49.11.47214732.2005.

Feldman, Morris E., et al., "Active-Site Inhibitors of mTOR Target Rapamycin-Resistant Outputs of mTORCI and mTORC2", "PLoS Biology", Feb. 10, 2009, pp. 0371-0383, vol. 7, No. 2, Publisher: Public Library of Science, Published in: doi:10.1371/journal.pbio. 1000038.

Gilliam, Bruce L., et al., "Rapamycin Reduces CCR5 mRNA Levels in Macaques: Potential Applications in HIV-1 Prevention and Treatment", "AIDS", Oct. 1, 2007, pp. 2108-2110, vol. 21, No. 15, Publisher: Lippincott Williams & Wilkins, Published in: http://journals.lww.com/aidsonline/Fulltext/2007/10010/Rapamycin_reduces_CCR5_mRNA_levels_in_macaques_.16.aspx.

Gravina, Giovanni Luca, et al., "Torc1/Torc2 Inhibitor, Palomid 529, Enhances Radiation Response Modulating CRM1-Mediated Survivin Function and Delaying DNA Repair in Prostate Cancer Models", "The Prostate", Apr. 8, 2014, pp. 852-868, vol. 74, No. 8, Publisher: Wiley Periodicals Inc., Published in: DOI 10.1002/pros. 22804.

Hattori, Shinichiro, et al., "Potent Activity of a Nucleoside Reverse Transcriptase Inhibitor, 4'-Ethynyl-2-Fluoro-2'-Deoxyadenosine, against Human Immunodeficiency Virus Type 1 Infection in a Model . . .", "Antimicrobial Agents and Chemotherapy", Sep. 1, 2009, pp. 3887-3893, vol. 53, No. 9, Publisher: American Society for Microbiology, Published in: doi:10.1128/AAC.00270-09.

Heredia, A., et al., "Rapamycin Causes Down-Regulation of CCR5 and Accumulation of Anti-HIV Beta-Chemokines: An Approach to Suppress R5 Strains of HIV-1", "PNAS", Jul. 8, 2003, pp. 10411-10416, vol. 100, No. 18, Publisher: National Academy of Sciences, Published in: www.pnas.org/cgi/doi/10.1073/pnas.1834278100.

Heredia, Alonso, et al., "Rapamycin Reduces CCR5 Density Levels on CD4 T Cells, and This Effect Results in Potentiation of Enfuvirtide (T-20) against R5 Strains of Human Immunodeficiency Virus Type 1 In Vitro", "antimicrobial Agents and Chemotherapy", Jul. 1, 2007, pp. 2489-2496, vol. 51, No. 7, Publisher: American Society for Microbiology, Published in: doi:10.1128/AAC.01602-06.

Heredia, Alonso, et al., "Reduction of CCR5 with Low-Dose Rapamycin Enhances the Antiviral Activity of Vicrivirocagainst Both Sensitive and Drug-Resistant HIV-1", "PNAS", Oct. 27, 2008, pp. 20476-20481, vol. 105, No. 51, Publisher: National Academy of Sciences of the USA, Published in: www.pnas.org/cgi/doi/10.1073/pnas.0810843106.

Hsieh, Andrew C., et al., "The Translational Landscape of mTOR Signalling Steers Cancer Initiation and Metastasis", "Nature", May 3, 2012, pp. 55-61, vol. 485, No. 7396, Publisher: Macmillan Publishers Ltd., Published in: www.nature.com/doifinder/10.1038/nature10912.

Janes, Matthew R., et al., "Effective and Selective Targeting of Leukemia Cells Using a TORC1/2 Kinase nhibitor", "Nature Medicine", Feb. 1, 2010, pp. 205-213, vol. 16, No. 2, Publisher: Nature America Inc., Published in: doi:10.1038/nm.2091.

Liao, Hui, et al., "Dramatic antitumor effects of the dual mTORCI and mTORC2 inhibitor AZD2014 in hepatocellular carcinoma", "Am J Cancer Res", Jan. 1, 2015, pp. 125-139, vol. 5, No. 1, Publisher: Am J Cancer Res, Published in: www.ajcr.us /ISSN:2156-6976/ajcr0003046.

Nicoletti, F., et al., "Inhibition of human immunodeficiency virus (HIV-1) infection in human peripheral blood eucocytes-SCID reconstituted mice by rapamycin", "Clinical and Experimental Immunology", Sep. 1, 2008, pp. 28-34, vol. 155, No. 1, Publisher: British Society for Immunology, Published in: doi:10.1111/J.1365-2249. 2008.03780.

Platt, Emily J., et al., "Effects of CCR5 and CD4 Cell Surface Concentrations on Infections by Macrophagetropic solates of Human Immunodeficiency Virus Type 1", "Journal of Virology", Apr. 1, 1998, pp. 2855-2864, vol. 72, No. 4, Publisher: American Society for Microbiology, Published in: http://jvi.asm.org/.

Reynes, Jacques, et al., "CD4+ T Cell Surface CCR5 Density as a Determining Factor of Virus Load in Persons nfected with Human Immunodeficiency Virus Type 1", "Journal of Infectious Diseases", Mar. 8, 2000, pp. 927-932, vol. 181, No. 3, Publisher: Infectious Diseases Society of America, Published in: 0022-1899/2000/18103-0016$02.00.

Reynes, Jacques, et al., "CD4 T cell surface CCR5 density as a host factor in HIV-1 disease progression", "AIDS", May 2, 2001, pp. 1627-1634, vol. 15, No. 13, Publisher: Lippincott Williams & Wilkins, Published in http://www.ncbi.nlm.nih.gov/pubmed/11546936.

Simioni, Carolina, et al., "Activity of the novel mTOR inhibitor Torin-2 in B-precursor acute lymphoblastic eukemia and its therapeutic potential to prevent Akt reactivation", "Oncotarget", Sep. 16, 2014, pp. 10034-10047, vol. 5, No. 20, Publisher: Impact Journals, Published in: www.impactjournals.com/oncotarget/.

Slotkin, Emily K., et al., "MLN0128, an ATP-Competitive mTOR Kinase Inhibitor with Potent In Vitro and In Vivo Antitumor Activity, as Potential Therapy for Bone and Soft-Tissue Sarcoma", "Mol Cancer Ther", Feb. 1, 2015, pp. 395-406, vol. 14, No. 2, Publisher: American Association for Cancer Research, Published in: doi 10.1158/1535-7163.MCT-14-0711.

Takeuchi, Craig S., et al., "Discovery of a Novel Class of Highly Potent, Selective, ATP-Competitive, and Orally Bioavailable Inhibitors of the Mammalian Target of Rapamycin (mTOR)", "J. of Medical Chemistry", Feb. 8, 2013, pp. 2218-2234, vol. 56, No. 6, Publisher: American Chemical Society, Published in: dx.doi.org/10.1021/jm3007933.

Thoreen, Carson C., et al., "An ATP-competitive Mammalian Target of Rapamycin Inhibitor Reveals Rapamycin-resistant Functions of mTORC1", "J. of Biological Chemistry", Jan. 15, 2009, pp. 8023-8032, vol. 284, No. 12, Publisher: American Society for Biochemistry and Molecular Biology, Inc, Published in: DOI 10.1074/jbc. M900301200.

Venkatesha, Venkatasubbaiah A., et al., "P7170, a novel inhibitor of mTORC1/mTORC2 and Activin receptor-like Kinase 1 (ALK1) inhibits the growth of non small cell lung cancer", "Molecular Cancer", Dec. 2, 2014, pp. 259-269, vol. 13, No. 1, Publisher: BioMed Central, Published in: http://www.molecular-cancer.com/content/13/1/259.

Celum, C., et al., "Acyclovir and Transmission of HIV-1 from Persons Infected with HIV-1and HSV-2," N. Engl. J. Med., Feb. 4, 2010, pp. 427-439, vol. 362.

Liu et al. Discovery of 9-(6-aminopyridin-3-yl)-1-(3-(trifluormethyl)-phenyl)benzo[h][1,6]naphthyridin-2(1 H)-one (Torin2) as a potent selective, and orally available mammalian target of rapamycin (mTOR) inhibitor for treatment of cancer, J. Med. Chem. 2011, vol. 54, pp. 1473-1480.

Knight et al. Discovery of GSK2126458, a highly potent inhibitor of PI3K and Mammalian target of rapamycin, ACS Med. Chem. Lett. 2010, vol. 1, pp. 39-43.

Pike et al. "Optimization of potent and selective dual mTORCI and mTORC2 inhibitors: the discovery of AZD8055 anti AZD2014," Bioorganic & Medicinal Chemistry Letters, 2012, vol. 23, pp. 1212-1216.

Dittmer et al. "Determinants of mTOR inhibitor therapy in AIDS-associated malignancies," Infectious Agents and Dancer, 2012, vol. 7, Suppl. 1, 09. (Year: 2012).

Nicoletti et al. "mTOR as a multifunctional therapeutic target in HIV infection," Drug Discovery Today, 2011, vol. 16, No. 15/16, pp. 715-721. (Year: 2011).

(56) References Cited

OTHER PUBLICATIONS

Heredia et al., Targeting of mTOR catalytic site inhibits multiple steps of the HIV-1 lifecycle and suppresses HIV-1 viremia in humanized mice, PNAS, 2015, PNAS, vol. 112 No. 30 pp. 9412-9417.
Besnard et al., The mTOR Complex Controls HIV Latency, Cell Host & Microbe 20, 2016, pp. 785-797.

* cited by examiner

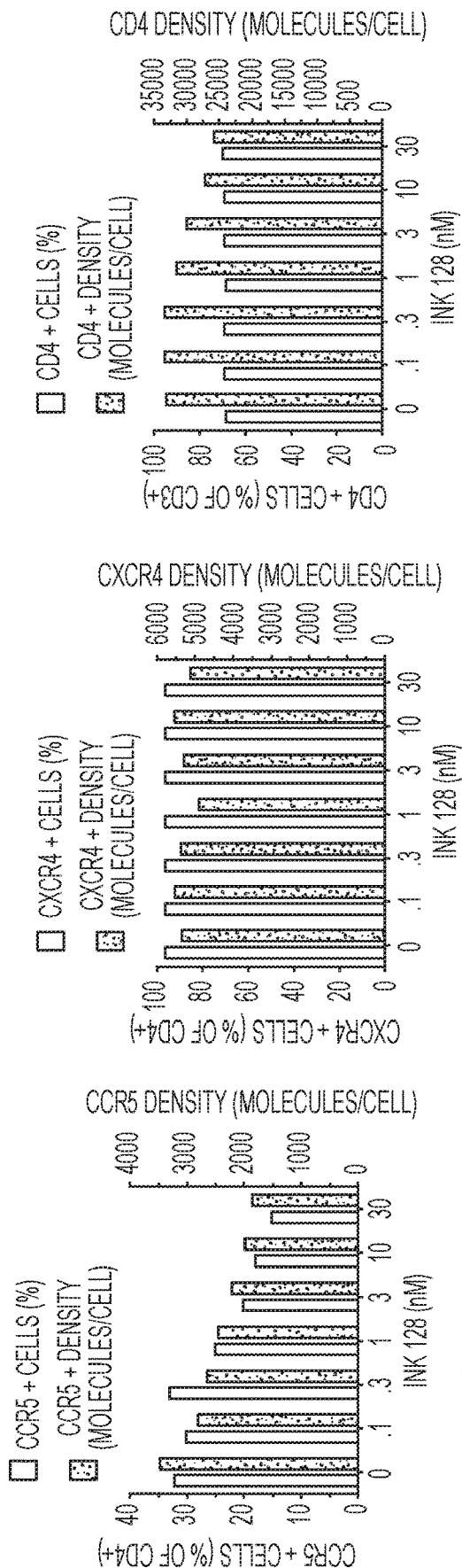

TREATMENT AGENTS FOR INHIBITING HIV AND CANCER IN HIV INFECTED PATIENTS

CROSS REFERENCE TO RELATED APPLICATIONS

This application is a continuation application of Ser. No. 15/159,444 filed May 19, 2016 which claims the benefit of provisional application 62/163,408, entitled "A Single Treatment Agent for Inhibiting HIV and Cancer in HIV Infected Patients," filed May 19, 2015, the entire contents of which are incorporated herein.

BACKGROUND

Human Immunodeficiency Virus (HIV), the virus that causes AIDS, is one of the world's most serious health and development challenges. According to the World Health Organization (WHO) there were approximately 36.9 million people worldwide living with HIV/AIDS in 2014. Of these, 2.6 million were children (<15 years old).

In the United States, the CDC estimates that 1,218,400 persons aged 13 years and older are living with infection, including 156,300 (12.8%) who are unaware of their infection. Over the past decade, the number of people living with HIV has increased, while the annual number of new HIV infections has remained relatively stable. Still, the pace of new infections continues at far too high a level—particularly among certain groups. In 2013, an estimated 47,352 people were diagnosed with HIV infection in the United States. In that same year, an estimated 26,688 people were diagnosed with AIDS. Overall, an estimated 1,194,039 people in the United States have been diagnosed with AIDS.

Despite significant advances in the treatment of HIV infection with the use of antiretroviral therapies, a strong need for the development of alternative antiviral agents exists. The HIV virus has been difficult to treat in view of the emergence of drug-resistant viral strains, the need for sustained adherence to complex treatment regimens, and the toxicity of currently used antivirals agents.

SUMMARY

It has been discovered that certain mTOR inhibitors (e.g., INK128, Torin-2, GSK2126458, and AZD2014)128 and Torin-2) are effective in treatment of the HIV virus as well as in HIV-infected subjects diagnosed with cancer. In certain embodiments, methods are provided for treating the HIV virus and cancer in a subject in need by administering to the subject a therapeutically effective amount of an mTOR inhibitor. The mTOR inhibitor is selected from the group consisting of INK128, GSK2126458, AZD2014, and Torin-2. Preferably, the mTOR inhibitor is INK128 or Torin-2.

INK128 is administered in certain embodiments in a therapeutically effective amount from about 0.5 mg to about 4 mg to achieve a plasma concentration of about 200 nM in the subject. Torin-2 may be administered in a therapeutically effective amount from 0.05 mg to about 10 mg. GSK2126458 is administered in a therapeutically effective amount from 0.05 mg to about 0.25 mg in certain embodiments. In other embodiments, AZD2014 is administered in a therapeutically effective amount from 5 mg to about 50 mg.

The mTOR inhibitor (e.g., INK128, Torin-2, GSK2126458, and AZD2014)128 or Torin-2) may be administered orally, intravenously, intramuscularly, intrathecally, or subcutaneously, sublingually, buccally, rectally, vaginally, by ocular route or by otic route, nasally, by inhalation, by nebulization, cutaneously, topically or systemically, and transdermally in certain embodiments.

In other embodiments, the mTOR inhibitor (e.g., INK128, Torin-2, GSK2126458, and AZD2014)128 or Torin-2) is administered alone, or in combination with a second mTOR inhibitor or a second antiretroviral agent. The mTOR inhibitor and the second antiretroviral agent are administered at the same time, at different times, or sequentially in certain embodiments. The second antiretroviral agent may be selected from the group consisting of CCR5 antagonists, reverse transcriptase inhibitors, integrase inhibitors, protease inhibitors, and any combination thereof. The mTOR inhibitor and the second antiretroviral agent can also be administered in combination with a cancer therapeutic agent selected from the group consisting of DNA damaging agents, microtubule agents, and signal transduction agents. For example, the cancer therapeutic agents are selected from the group consisting of carboplatin, BCNU, cytosine arabinoside, paclitaxel, vinblastine, sorafenib, pazopanib, erlotinib, and imatinib.

In certain embodiments, the type of cancer is selected from the group consisting of non-small cell lung, small cell lung, prostate, breast, liver, Hodgkin lymphoma, non-Hodgkin lymphoma, Kaposi sarcoma, B cell acute lymphoblastic leukemia, bone sarcoma, and soft tissue sarcoma.

Methods of treating HIV in a subject in need thereof are also provided comprising administering to the subject a therapeutically effective amount of INK128 having a chemical structure described herein or Torin-2 having a chemical structure described herein or salts or hydrates thereof. INK128 may be administered in a therapeutically effective amount from about 0.5 mg to about 4 mg to achieve a plasma concentration of about 200 nM in the subject. Torin-2 may be administered in a therapeutically effective amount from about 0.05 mg to about 10 mg.

In other embodiments, the mTOR inhibitor (e.g., INK128, Torin-2, GSK2126458, and AZD2014)128 or Torin-2) is administered alone, or in combination with a second antiretroviral agent. The antiretroviral agent may be selected from the group consisting of an entry inhibitor, a reverse transcriptase inhibitor, a protease inhibitor and an integrase inhibitor. Preferably, the antiretroviral agent is selected from the group consisting of CCR5 antagonists, reverse transcriptase inhibitors, integrase inhibitors, protease inhibitors and any combination thereof. The antiretroviral agents are selected from the group consisting of maraviroc, efavirenz, raltegravir, indinavir, and any combination thereof.

The mTOR inhibitor and the second antiretroviral agent may be administered in combination with a cancer therapeutic agent selected from the group consisting of DNA damaging agents, microtubule agents, and signal transduction agents in certain embodiments. The cancer therapeutic agents are selected from the group consisting of: carboplatin, BCNU, cytosine arabinoside, paclitaxel, vinblastine, sorafenib, pazopanib, erlotinib, and imatinib.

Methods are provided in certain embodiments with a therapeutically effective amount of mTOR inhibitor that inhibits both R5 and X4 HIV replication. Other methods are provided with a therapeutically effective amount of mTOR inhibitor that inhibits entry of R5 HIV in vitro. In yet other methods, the therapeutically effective amount of mTOR inhibitor inhibits LTR gene expression.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1A is a diagram that illustrates the chemical structure of INK128. FIG. 1B is a graph illustrating the effect of INK128 on cell viability. PBLs from healthy donors were activated with antibodies against CD3 and CD8 for 3 days. Activated cells were cultured in medium containing IL-2 and the indicated concentrations of INK128 for 5 days. On day 5, cell viability was measured by MTT. FIG. 1C is a graph illustrating the effect of INK128 on HIV replication. Activated PBLs were infected with R5 HIV BaL or X4 HIV HXB2 for 2 hours using a MOI of 0.001. Infected cells were cultured in IL-2 medium and various dilutions of INK128. On day 7, virus production was measured by p24 ELISA in the culture supernatants according to an embodiment.

FIG. 3A-3B are bar graphs that shows cell-cell fusion between effector cells expressing R5 HIV JRFL Env or X4 HIV HXB2 Env and primary CD4+T target cells. FIG. 3C-3D are graphs that depict early products of reverse transcription (R/U5 region) in PBLs infected with R5 (JRFL) or X4 (HXB2) HIV and treated with INK128 for 16 hours FIG. 3E-3F are graphs that illustrates integrated HIV DNA in PBLs infected with R5 (JRFL) or X4 (HXB2) HIV and treated with INK128 for 72 hours according to an embodiment.

FIG. 4A-4C are bar graphs that reflect INK128's reduction of CCR5, but not CXCR4 or CD4, levels on PBLs. PBLs were cultured in IL-2 medium and various concentrations of INK128 for 7 days before Flow Cytometry Analysis. FIG. 4A and FIG. 4B represent measurement of CCR5 (FIG. 4A) and CXCR4 (FIG. 4B), where lymphocytes were first gated on CD3 and CD4. FIG. 4C is a bar graph that illustrates measurement of CD4 where lymphocytes were gated using CD3 in combination with CD8 Immunofluorescence intensity was measured as an estimate of the average number of molecules on the cell surface using Quantibrite-phycoerythrin (PE) beads according to an embodiment.

FIG. 7A is a graph illustrating mice weight at the beginning of experiment (day 0) and after 14 days of daily treatment (i.p.) with INK128. FIG. 7B is a graph that shows the comparison of changes in body weight (day 0 to day 14) between INK128-treated mice according to an embodiment.

Figure 1C:
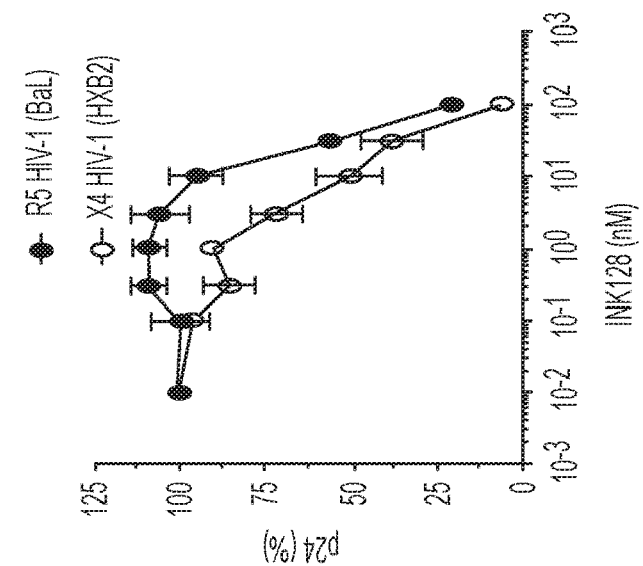
FIG. 1A-1C are representations that illustrate that INK128 inhibits replication of R5 HIV BaL and X4 HIV HXB2 in primary cells.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

DETAILED DESCRIPTION

It has been discovered that targeting an mTOR catalytic site with the mTORC1/mTORC2 inhibitor INK128 results in inhibition of multiple steps of the HIV-1 lifecycle and suppression of HIV-1 viremia in vivo. mTOR is a conserved serine/threonine kinase that forms two complexes, mTORC1 and mTORC2. The natural product isolated from *Streptomyces hygroscopicus* known as Rapamycin (*RAPA*, Rapamune, sirolimus) targets mTOR in mammals and is an allosteric mTOR inhibitor but only selectively inhibits mTORC1. In doing so, Rapamycin interferes with viral entry of CCR5 (R5)-tropic HIV and with basal transcription of the HIV LTR, potently inhibiting replication of R5 HIV but not CXCR4 (X4)-tropic HIV in primary cells.

In an effort to overcome this drawback, ATP-competitive mTOR kinase inhibitors (TOR-KIs) have been developed to inhibit both mTORC1 and mTORC2. Using INK128 as a prototype TOR-KI, it has been discovered that potent inhibition of both R5 HIV and X4 HIV in primary lymphocytes (EC50<50 nM) can occur in the absence of toxicity. Experimental results described herein demonstrate that INK128 inhibited R5 HIV entry by reducing CCR5 levels. INK128 also inhibited both basal and induced transcription of HIV genes, consistent with inhibition of mTORC2, whose activity is critical for phosphorylation of PKC isoforms and, in turn, induction of NF-κB. INK128 enhanced the antiviral potency of the CCR5 antagonist Maraviroc in a synergistic manner, and interacted favorably with antivirals such as HIV inhibitors of reverse transcriptase, integrase and protease. In vivo, INK128 decreased plasma HIV RNA by >2 $\log^{10}$ units and partially restored CD4/CD8 cell ratios. As a result, targeting of cellular mTOR with INK128 (and perhaps others TOR KIs, e.g., Torin-2) provides a strategy to inhibit HIV, especially in patients with drug resistant HIV strains.

1. Definitions

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and intended to be non-limiting. Furthermore, where the description of one or more embodiments uses the term "comprising," those skilled in the art would understand that, in some specific instances, the embodiment or embodiments can be alternatively described using the language "consisting essentially of" and/or "consisting of."

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are performed generally according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The term "administering" as used herein, means delivery, for example of an mTOR inhibitor alone, or in combination with a antiretroviral agent, or in further combination with a cancer therapeutic agent.

The term "cancer therapeutic agent" as used herein, means an anticancer agent, an antineoplastic agent, and antitumor agent, used in the treatment of HIV-infected subjects diagnosed with cancer.

The term "HIV," as used herein means a genetically related member of the Lentivirus genus of the Retroviridae family that shows a particular tropism for CD4+ T cells.

The term "HART", or "highly active antiretroviral treatment as used herein refers to a treatment consisting of a combination of different therapeutic agents that inhibit HIV replication.

The term "mTOR" or "Mechanistic Target of Rapamycin" as used herein means a serine/threonine protein kinase that regulates cell growth, cell proliferation, cell motility, cell survival, protein synthesis, autophagy, transcription. mTOR forms two conserved, structurally distinct kinase complexes termed mTOR complex 1 (mTORC1) and mTORC2. Each complex phosphorylates a different set of substrates to regulate cell growth.

The term "mTOR inhibitor" as used herein refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor. Preferable mTOR inhibitors include (i) INK128 (i.e., Sapanisertib, MLN0128) shown in FIG. 1A, having the molecular formula $C_{15}H_{15}N_7O$ identified as CAS No: 1224844-38-5, having the structure,

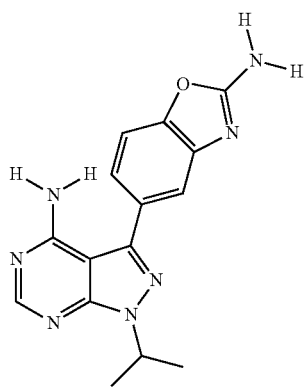 [SMILES: CC(C)n1nc(-c2ccc3oc(N)nc3c2)c2c(N)ncnc21]

(*Adapted from PubChem) (ii) Torin-2 a potent and selective inhibitor of cellular mTOR activity, having the molecular formula $C_{24}H_{15}F_3N_4O$ identified as CAS No: 1223001-51-1, and identified as 9-(6-Amino-3-pyridinyl)-1-[3-(trifluoromethyl)phenyl]-benzo[h]-1,6-naphthyridin-2(1H)-one, having the structure,

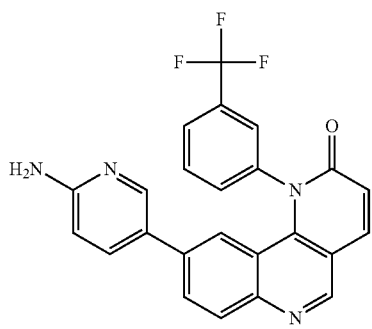 [SMILES: Nc1ccc(-c2ccc3ncc4ccc(=O)n(-c5cccc(C(F)(F)F)c5)c4c3c2)cn1]

(*Adapted from PubChem)
(iii) GSK2126458, having the chemical name, 2,4-Difluoro-N-{2-(methyloxy)-5-[4-(4-pyridazinyl)-6-quinolinyl]-3-pyridinyl}benzenesulfonamide (GSK2126458, 1) and identified as a highly potent, orally bioavailable inhibitor of PI3Kα and mTOR with in vivo activity in both pharmacodynamic and tumor growth efficacy models, having the structure,

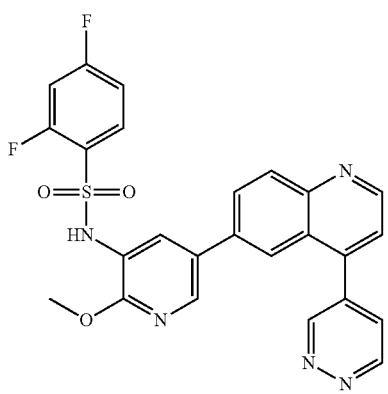 [SMILES: COc1ncc(-c2ccc3nccc(-c4ccnnc4)c3c2)cc1NS(=O)(=O)c1ccc(F)cc1F]

(*Adapted from PubChem),
and (iv) AZD2014, a potent (IC50 2.81 nM), selective (inactive against 220 other kinases) inhibitor of mTOR kinase, having the structure,

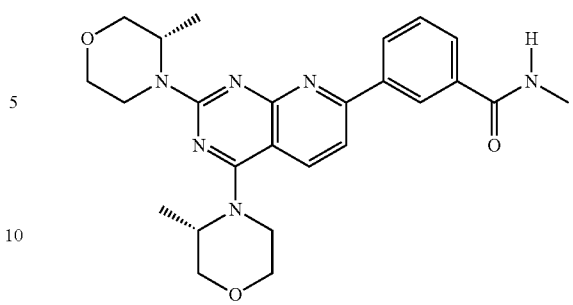

(*Adapted from PubChem).

The term "primary cells" as used herein refers to cells established for growth in vitro. Cells that are cultured directly from a subject are known as primary cells. With the exception of some derived from tumors, most primary cell cultures have limited lifespan.

The term "subject," as used herein refers to animals, such as mammals. For example, mammals contemplated include humans, primates, rats, mice, dogs, and cats. The terms "subject" and "patient" are used interchangeably.

The term "therapeutically effective amount" as used herein refers to an amount administered to achieve a therapeutic effect obtained by reduction, suppression, remission, or eradication of a disease state.

2. Overview

Antiretroviral agents have transformed HIV infection into a chronic condition that can require life-long therapy. Patients on therapy can fail treatment, among other factors, because of the emergence of drug resistance. In view of the drug resistance problem, a strong need exists for identification of therapeutic agents that can target and inhibit HIV through different cellular mechanisms. This need for the development of alternative antiretroviral agents is primarily due to drug resistance but also for sustained adherence to complex treatment regimens and toxicity of currently used antiviral drugs. Current antiretroviral agents against HIV target several different steps in the viral lifecycle (1, 2). However, there is a continuous need for novel classes of antiretroviral agents targeting additional stages of viral replication, primarily due to emergence of drug resistance (1, 3). There are currently several antiretroviral classes against reverse transcription, integration and maturation (4). Within each class, the availability of several drugs with distinct resistance profiles make it possible to switch to an alternative drug from the same class in the event of resistance.

In contrast, the HIV lifecycle steps of entry and transcription are underrepresented in current therapy. First, there are only two licensed entry inhibitors: the CCR5 antagonist Maraviroc (5) and the fusion inhibitor Enfuvirtide (6). However, the virus tropism specificity of Maraviroc (7) and the need for twice-daily s.c. injection of Enfuvirtide (8) limit their clinical potential. Second, there are no licensed inhibitors of HIV transcription. Therefore, new approaches for targeting entry and transcription may provide alternative treatment options for HIV-infected patients and HIV-infecting patients diagnosed with cancer, especially those with drug-resistant HIV strains.

mTOR

Targeting cellular proteins that HIV requires in its lifecycle is an attractive approach to overcome HIV drug resistance because cellular proteins have lower mutations rates than do HIV proteins under drug pressure, and because there are so many host proteins needed by HIV for its replication. A downside, of course, is the possibility of side effects from inhibition of a cellular protein.

One mode of potential attack is the targeting of cellular proteins that HIV requires in its lifecycle to help overcome HIV drug resistance because cellular proteins have lower mutation rates than do HIV proteins. mTOR is a serine/threonine protein kinase that regulates cell growth, cell proliferation, cell motility, cell survival, protein synthesis, autophagy, and transcription. mTOR belongs to the phosphatidylinositol 3-kinase-related kinase protein family, and fibrosis. As previously discussed, mTOR comprises two complexes-mTORC1 and mTORC2—which are involved in regulating protein translation and transduction signaling. mTORC1 promotes translation initiation and synthesis of cellular proteins whereas mTORC2 regulates full activation of the AKT pathway and also regulates PKC signaling.

HIV-1 Co-Receptors CCR5 and CXCR4

HIV entry into target cells occurs by a multi-step process that culminates with the fusion of viral and cellular membranes. HIV-1 utilizes CD4 as its primary receptor. HIV tropism (the type of CD4 cell that the virus will be able to infect) is determined by the type of coreceptor recognized by gp120. Binding to CCR5 is known as CCR5 (or R5) tropism, while binding to CXCR4 is known as CXCR4 (or X4) tropism. Binding to CD4 is followed by conformational changes in the viral envelope that lead to the engagement of one of the viral co-receptors (CCR5 or CXCR4). Based on their functionality in vitro, other chemokine receptors may also work as HIV-1 co-receptors. CCR5 and CXCR4 constitute the major co-receptors in vivo. The observation that high level of CCR5 expression on CD4-positive primary T cells is associated with high viral loads and accelerated disease progression further highlights the contribution of CCR5 to disease progression.

Rapamycin, which targets mTORC1 but not mTORC2 (10), interferes with the HIV steps of CCR5-mediated entry and with basal (but not induced) transcription of the HIV LTR (11-14). These activities of rapamycin effectively inhibit replication of CCR5 (R5)-tropic HIV, but not CXCR4 (X4)-tropic HIV, in primary lymphocytes (11, 13, 15). The recently developed ATP-competitive mTOR kinase inhibitors (TOR-KIs) inhibit both mTORC1 and mTORC2 complexes (16-19). mTORC1 controls CCR5 expression and basal HIV transcription (11-13), and because mTORC2 controls phosphorylation of PKC (9, 20-22), required for NF-κB induction of HIV transcription (23, 24).

3. Embodiments

Most HIV antiretroviral agents target viral proteins. Unfortunately, HIV mutates under drug pressure, which can lead to drug resistance. Targeting cellular proteins that HIV requires in its lifecycle may help overcome HIV drug resistance because cellular proteins have lower mutations rates than do HIV proteins. Methods are provided for treatment of HIV infected subjects diagnosed with cancer with an mTOR inhibitor. Other methods are provided for treatment of HIV using the mTOR inhibitor INK128, Torin-2, GSJ 2126458, or AZD2014. The present inventors demonstrate that dual targeting of mTORC-1/2 with the catalytic inhibitor INK128 blocks HIV by interfering with entry and with transcription (basal and induced). Importantly, INK128 suppressed HIV in a preclinical animal model, suggesting that mTORC-1/2 catalytic inhibitors may help control HIV in patients, particularly in those patients diagnosed with cancer and with drug-resistant HIV.

A. Methods of Treatment

Subjects with HIV and Cancer

Patients undergoing long-term drug therapies (e.g., highly active antiretroviral therapy treatment) are at a higher risk of various HIV-related complications. Hyperactivation of mTOR has been found to contribute to dysregulated apoptosis and autophagy which determine CD4+-T-cell loss, impaired function of innate immunity and development of neurocognitive disorders. Dysregulated mTOR activation has also been shown to play a key part in the development of nephropathy and in the pathogenesis of HIV-associated malignancies. These studies strongly support a multifunctional key role for mTOR in the pathogenesis of HIV-related disorders and suggest that specific mTOR inhibitors could represent a novel approach for the prevention and treatment of these pathologies. In one embodiment, methods are provided for treating a subject infected with HIV and diagnosed as having cancer with a therapeutically effective amount of an mTOR inhibitor (e.g., INK128, Torin-2, GSK2126458, and AZD2014) as described in, but not limited to those in Table 1 and Table 2.

mTOR Inhibitors

Currently two classes of mTOR inhibitors exist: allosteric inhibitors (Table 1) and catalytic inhibitors (Table 2).

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

TABLE 1

| Allosteric mTOR Inhibitors | |
|---|---|
| Compound | Chemical Name (IUPAC) |
| Rapamycin (sirolimus) AY-22989 | 40-[3-hydroxy-2-(hydroxymethyl)-2-methylpropanoate] |
| Rapamycin (temsirolimus) CCT779 | (1R,2R,4S)-4-{(2R)-2-R3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate |

TABLE 1-continued

Allosteric mTOR Inhibitors

| Compound | Chemical Name (IUPAC) |
|---|---|
| Ridaforolimus (AP-23573/MK-8669) | 1R,2R,4S)-4-R2R)-2-[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04,9]hexatriaconta-16,24,26,28-tetraen-12-yl]propyl]-2-methoxycyclohexyl dimethylphosphinate |
| Rapamycin derivatives (e.g., everolimus) | dihydroxy-12-[(2R)-1-[ (1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone |
| Rapamycin analogs (rapalogs) | Various |
| Zotarolimus (ABT578) | (3S,6R,7E,9R,10R,12R,14S,15E,17E,19E,21S,23S,26R,27R,34aS)-9,27-dihydroxy-10,21-dimethoxy-3-{(1R)-2-[(1S,3R,4S)-3-methoxy-4-(1H-tetrazol-1-yl)cyclohexyl]-1-methylethyl}-6,8,12,14,20,26-hexamethyl-4,9,10,12,13,14,21,22,23,24,25,26,27,32,33,34,34a-heptadecahydro-3H-23,27-epoxypyrido[2,1-c][1,4]oxazacyclohentriacontine-1,5,11,28,29(6H,31H)-pentone |
| Umirolimus | Various |

*Adapted from PubChem

Alternatively or additionally, catalytic, ATP-competitive mTOR inhibitors have been found to target the mTOR kinase domain directly and target both mTORC1 and mTORC2. These are also more complete inhibitors of mTORC1 than such allosteric mTOR inhibitors as rapamycin, because they modulate rapamycin-resistant mTORC1 outputs such as 4EBP1-T37/46 phosphorylation and cap-dependent translation.

TABLE 2

Catalytic mTOR Inhibitors

| Compound | Chemical Name |
|---|---|
| INK-128 Sapanisertib, MLN0128 | 5-(4-amino-1-propan-2-ylpyrazolo[3,4-d]pyrimidin-3-yl)-1,3-benzoxazol-2-amine |
| BEZ235 | 2-methyl-2-[4-(3-methyl-2-oxo-8-quinolin-3-yl-2,3-dihydro-imidazo[4,5-c]quinolin-1-yl)-phenyl]-propionitrile |
| AZD2014 | 3-[2,4-bis[(3S)-3-methylmorpholin-4-yl]pyrido[2,3-d]pyrimidin-7-yl]-N-methylbenzamide |
| PKI-587 | 1-[4-[4-(dimethylamino)piperidine-1-carbonyl]phenyl]-3-[4-(4,6-dimorpholino-1,3,5-triazin-2-yl)phenyl]urea |
| GSK-2126458 | 2,4-difluoro-N-{2-methoxy-5-[4-(4-pyridazinyl)-6-quinolinyl]-3-pyridinyl}benzenesulfonamide |
| TORIN 2 | 9-(6-Amino-3-pyridinyl)-1-[3-(trifluoromethyl)phenyl]-benzo[h]-1,6-naphthyridin-2(1H)-one |
| PALOMID 529 | 8-(1-Hydroxyethyl)-2-methoxy-3-((4-methoxybenzypoxy)-6H-benzo[c]chromen-6-one |

*Adapted from PubChem

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTOR inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof.

mTOR inhibitors such as INK128 are useful in cancer therapy where mTOR is upregulated. Unfortunately, a growing population of HIV infected patients with cancer exists. HIV-infected patients with cancer potentially face a higher cancer-specific mortality compared to those without HIV. Recent literature suggests that cancer-specific mortality was significantly higher in HIV-infected patients for a variety of cancers, including colorectal, pancreatic, laryngeal, lung, melanoma, breast and prostate. There is a pressing need to identify mTOR agents that can target and inhibit HIV entry and transcription as well as aid in treating those HIV patients with cancer. Identification of such mTOR inhibitors would provide an approach for concomitant treatment of HIV and cancer without having to disrupt anti-HIV therapy in HIV infected patients with certain kinds of cancers. Such an approach would simplify treatment by reducing the number of therapeutic agents administered and avoiding the potentially detrimental interactions between cancer drugs and HIV drugs.

HIV Infected Subjects

In certain embodiments, methods are provided for treating a subject infected with HIV by administering a therapeutically effective amount of the mTOR inhibitor INK128, Torin-2, GSJ 2126458, or Torin-2). In a preferred aspect mTOR targets HIV and (i) inhibits its entry into the cell, (ii) inhibits LTR gene expression, (iii) inhibits replication, and thereby treats HIV-infected subjects. Identification of mTOR agents that provide an approach for treating subjects infected with HIV is desirable. Therefore, methods of inhibiting entry of R5 HIV in vitro, methods of inhibiting HIV LTR gene expression, and methods of inhibiting R4 and X4 HIV replication are provided by administering the mTOR inhibitor INK128.

It has been discovered that INK128 inhibits entry of R5, but not X4, HIV in primary lymphocytes. Unlike rapamycin, the newly developed TOR-KIs including INK128 inhibit both mTORC1 and mTORC2. Where INK128 is used, inhibition of CCR5 expression and inhibition of R5 HIV entry were demonstrated. Methods are provided in certain embodiments for inhibiting R5 and X4 HIV replication by administering a therapeutically effective amount of the mTOR inhibitor INK128.

In other embodiments, INK128 potently inhibited basal transcription as well as transcription induced by PMA and by Tat. This broad anti-transcriptional activity of INK128 is consistent with inhibition of mTORC2, whose activity is important for phosphorylation of PKC isoforms (including isoforms α and θ) (9, 20-22), and, in turn, induction of NF-κB. By interfering with NF-κB induction, INK128 may prevent recruitment of the host transcription factor P-TEFb to the HIV LTR, thereby decreasing virus transcription. In infectivity assays using primary PBLs, INK128 inhibited both R5 and X4 HIV, laboratory-adapted and primary isolates, with EC50 values <50 nM. Moreover, INK128 enhanced the antiviral potency of the CCR5 antagonist Maraviroc, probably by decreasing CCR5 levels, and had favorable antiviral interactions with inhibitors of reverse transcription, integration and protease.

Administration of INK128 in the present invention reduces plasma viremia by more than 2 $\log^{10}$ units in humanized mice. This magnitude of virus suppression is similar to that achieved by EFdA, a potent NRTI in clinical development, in humanized mice (38). Thus, INK128, and perhaps other TOR-KIs, may have anti-HIV activity in vivo. A counterintuitive, yet important, property of TOR-KIs is that their inhibition of both mTORC1 and mTORC2 is better tolerated by normal PBLs than targeting of mTORC1 alone with allosteric inhibitors.

Without being bound by theory, it is possible that mTOR may have a noncatalytic scaffolding function that is suppressed by allosteric inhibition, but not with the catalytic inhibitor. It is also possible that catalytic inhibitors may have a more transient effect on blocking the kinase activity of mTOR, sufficient for anti-HIV activity but not for cellular toxicity. The data reflect that INK128 did not decrease proliferation of primary PBLs at concentrations of up to 1 µM in the assays. Moreover, daily administration of INK128 inhibited HIV viremia in humanized mice without obvious toxicity, as determined by changes in body weight, over a 2-wk period. Mechanistically, mTOR controls host protein synthesis mainly at the translation level (9). In the present invention, TOR-KI inhibition of HIV gene expression occurs at the transcription level, suggesting an indirect effect of the drug.

B. Combination Treatments

Antiretroviral agents are referred to as ARV. Combination ARV therapy (cART) is referred to as highly active ART (HAART). It has been discovered that the mTOR inhibitor INK128 has favorable drug interactions with current antiretroviral classes that target the HIV lifecycle steps of entry, reverse transcription, integration, and maturation. Therefore, in certain aspects, antiretroviral agents (Table 3) or cancer therapeutic agents (Table 4) in combination with INK128 (or other mTOR inhibitors) are preferred because they increase the antiviral potency of current antiretroviral regimens. Each type, or "class," of ARV drugs attacks HIV in a different way.

In some embodiments, it may be advantageous to administer an mTOR inhibitor, e.g., an mTOR inhibitor described herein, with one or more therapeutic agents, preferably a second antiretroviral agent, and/or a second cancer therapeutic agent. For example, synergistic effects can occur with other antiretroviral agents, other cancer therapeutic agents.

Suitable therapeutic agents are known to one of ordinary skill in the art and can be found listed in the Physicians' Desk Reference.

Antiretroviral Agents

The first class of anti-HIV drugs was the nucleoside reverse transcriptase inhibitors (also called NRTIs or "nukes".) These drugs block the step, where the HIV genetic material is used to create DNA from RNA. The following antiretroviral agents preferable in certain embodiments in this class include but are not limited to those set forth in Table 3.

TABLE 3

| Antiretroviral Agents. |
|---|
| Nucleoside reverse transcriptase inhibitors (NRTIs, nukes) |
| Zidovudine (Retrovir, AZT) |
| Didanosine (Videx, Videx EC, ddI) |
| Stavudine (Zerit, d4T) |
| Lamivudine (Epivir, 3TC) |
| Abacavir (Ziagen, ABC) |
| Tenofovir, a nucleotide analog (Viread, TDF) |
| Combivir (combination of zidovudine and lamivudine) |
| Trizivir (combination of zidovudine, lamivudine and abacavir) |
| Emtricitabine (Emtriva, FTC) |
| Truvada (combination of emtricitabine and tenofovir) |
| Epzicom (combination of abacavir and lamivudine) |
| Non-nucleoside reverse transcriptase inhibitors (non-nukes, NNRTIs) |
| Nevirapine (Viramune, NVP) |
| Delavirdine (Rescriptor, DLV) |
| Efavirenz (Sustiva or Stocrin, EFV, also part of Atripla) |
| Etravirine (Intelence, ETR) |
| Rilpivirine (Edurant, RPV, also part of Complera or Epivlera). |
| Protease inhibitors (PIs) |
| Saquinavir (Invirase, SQV) |
| Indinavir (Crixivan, IDV) |
| Ritonavir (Norvir, RTV) |
| Nelfinavir (Viracept, NFV) |
| Amprenavir (Agenerase, APV) |
| Lopinavir/ritonavir (Kaletra or Aluvia, LPV/RTV) |
| Atazanavir (Reyataz, ATZ) |
| Fosamprenavir (Lexiva, Telzir, FPV) |
| Tipranavir (Aptivus, TPV) |
| Darunavir (Prezista, DRV) |
| Entry inhibitors (Enfuvirtide, Fuzeon, ENF, T-20) |
| Maraviroc (Selzentry or Celsentri, MVC) |
| HIV integrase inhibitors |
| Raltegravir (Isentress, RAL) |
| Elvitegravir (EVG, part of the combination Stribild) |
| Dolutegravir (Tivicay, DTG) |

Cancer Therapeutic Agents

The decision to use cancer therapeutic agents (e.g., anti-cancer antineoplastic, and antitumor), such as DNA damaging agents, microtubule agents, and signal transduction agents used in the treatment of HIV-infected subjects diagnosed with cancer (Table 4) depends on the type of tumor to be treated, the stage of malignancy, the condition of the subject, and financial considerations. In certain embodiments, cancer may be non-small cell lung cancer, small cell lung cancer, prostate cancer, breast cancer, liver cancer, Hodgkin lymphoma, non-Hodgkin lymphoma, Kaposi sarcoma, B cell acute lymphoblastic leukemia, bone sarcoma, and soft tissue sarcomas. Chemotherapy can be used as an adjuvant to surgery and irradiation and can be administered immediately after or before the primary treatment. Neoadjuvant therapy is administered before surgery or irradiation and is intended to improve the effectiveness of the primary therapy by possibly decreasing tumor size, stage of malignancy, or the presence of micro metastatic lesions. Responses to cancer chemotherapy can range from palliation (remission of secondary signs, generally without increase in survival time) to complete remission (in which clinically detectable tumor cells and all signs of malignancy are absent). The percentage and duration of complete remissions are criteria for the success of a particular chemotherapeutic protocol.

TABLE 4

| Cancer Therapeutic Agents | | | |
|---|---|---|---|
| Abiraterone Acetate | ABVD | Hydroxyurea | Omacetaxine Mepesuccinate |
| Abitrexate (Methotrexate) | ABVE | Hyper-CVAD | Oncaspar (Pegaspargase) |
| Abraxane (Paclitaxel Albumin-stabilized Nanoparticle Formulation) | ABVE-PC | Ibrance (Palbociclib) | Ondansetron Hydrochloride |
| AC | Afatinib Dimaleate | Ibritumomab Tiuxetan | Onivyde (Irinotecan Hydrochloride Liposome) |
| AC-T | Afinitor (Everolimus) | Ibrutinib | Ontak (Denileukin Diftitox) |
| Adcetris (Brentuximab Vedotin) | Akynzeo (Netupitant and Palonosetron Hydrochloride) | ICE | Opdivo (Nivolumab) |
| ADE | Alecensa (Alectinib) | Iclusig (Ponatinib Hydrochloride) | OPPA |
| Ado-Trastuzumab Emtansine | Alectinib | Idamycin (Idarubicin Hydrochloride) | Osimertinib |
| Adriamycin (Doxorubicin | Alemtuzumab | Idarubicin Hydrochloride | Oxaliplatin |
| Aldara (Imiquimod) | Alkeran for Injection (Melphalan Hydrochloride) | Idelalisib | Paclitaxel |
| Aldesleukin | Alkeran Tablets (Melphalan) | Ifex (Ifosfamide) | Paclitaxel Albumin-stabilized Nanoparticle Formulation |
| Aloxi (Palonosetron Hydrochloride) | Alimta (Pemetrexed Disodium) | Ifosfamide | PAD |
| Ambochlorin (Chlorambucil) | Anastrozole | Ifosfamidum (Ifosfamide) | Palbociclib |
| Amboclorin (Chlorambucil) | Aprepitant | IL-2 (Aldesleukin) | Palifermin |
| Aminolevulinic Acid | Aredia (Pamidronate Disodium) | Imatinib Mesylate | Palonosetron Hydrochloride |
| Arsenic Trioxide | Arimidex (Anastrozole) | Imbruvica (Ibrutinib) | Palonosetron Hydrochloride and Netupitant |
| Arzerra (Ofatumumab) | Aromasin (Exemestane) | Imiquimod | Pamidronate Disodium |
| Asparaginase Erwinia chrysanthemi | Arranon (Nelarabine) | Imlygic (Talimogene Laherparepvec) | Panitumumab |
| Avastin (Bevacizumab) | Axitinib | Inlyta (Axitinib) | Panobinostat |
| BEP | Azacitidine | Interferon Alfa-2b, Recombinant | Paraplat (Carboplatin) |
| Bevacizumab | BEACOPP | Interleukin-2 (Aldesleukin) | Paraplatin (Carboplatin) |
| Bexarotene | Becenum (Carmustine) | Intron A (Recombinant Interferon Alfa-2b) | Pazopanib Hydrochloride |
| Bexxar (Tositumomab and Iodine I 131 Tositumomab) | Beleodaq (Belinostat) | Iodine I 131 Tositumomab and Tositumomab | PCV |

TABLE 4-continued

| Cancer Therapeutic Agents | | | |
|---|---|---|---|
| Bicalutamide | Belinostat | Ipilimumab | Pegaspargase |
| BiCNU (Carmustine) | Bendamustine Hydrochloride | Iressa (Gefitinib) | Peginterferon Alfa-2b |
| Bleomycin | Bortezomib | Irinotecan Hydrochloride | PEG-Intron (Peginterferon Alfa-2b) |
| Blinatumomab | Bosulif (Bosutinib) | Irinotecan Hydrochloride Liposome | Pembrolizumab |
| Blincyto (Blinatumomab) | Bosutinib | Istodax (Romidepsin) | Pemetrexed Disodium |
| Busulfex (Busulfan) | Brentuximab Vedotin | Ixabepilone | Perjeta (Pertuzumab) |
| Cabazitaxel | Busulfan | Ixazomib Citrate | Pertuzumab |
| Cabozantinib-S-Malate | Capecitabine | Ixempra (Ixabepilone) | Platinol (Cisplatin) |
| CAF | CAPDX | Jakafi (Ruxolitinib Phosphate) | Platinol-AQ (Cisplatin) |
| Campath (Alemtuzumab) | Carac (Fluorouracil--Topical) | Jevtana (Cabazitaxel) | Plerixafor |
| Camptosar (Irinotecan Hydrochloride) | Carboplatin | Kadcyla (Ado-Trastuzumab Emtansine) | Pomalidomide |
| CARBOPLATIN-TAXOL | CEM | Keoxifene (Raloxifene Hydrochloride) | Pomalyst (Pomalidomide) |
| Carfilzomib | Ceritinib | Kepivance (Palifermin) | Ponatinib Hydrochloride |
| Carmubris (Carmustine) | Cerubidine (Daunorubicin Hydrochloride) | Keytruda (Pembrolizumab) | Portrazza (Necitumumab) |
| Carmustine | Cervarix (Recombinant HPV Bivalent Vaccine) | Kyprolis (Carfilzomib) | Pralatrexate |
| Carmustine Implant | Cetuximab | Lanreotide Acetate | Prednisone |
| Casodex (Bicalutamide) | Chlorambucil | Lapatinib Ditosylate | Procarbazine Hydrochloride |
| CeeNU (Lomustine) | CHLORAMBUCIL-PREDNISONE | Lenalidomide | Proleukin (Aldesleukin) |
| Cisplatin | CHOP | Lenvatinib Mesylate | Prolia (Denosumab) |
| Clafen (Cyclophosphamide) | COPDAC | Lenvima (Lenvatinib Mesylate) | Promacta (Eltrombopag Olamine) |
| Clofarabine | COPP | Letrozole | Provenge (Sipuleucel-T) |
| Clofarex (Clofarabine) | COPP-ABV | Leucovorin Calcium | Purinethol (Mercaptopurine) |
| Clolar (Clofarabine) | Cosmegen (Dactinomycin) | Leukeran (Chlorambucil) | Purixan (Mercaptopurine) |
| CMF | Cotellic (Cobimetinib) | Leuprolide Acetate | Radium 223 Dichloride |
| Cobimetinib | Crizotinib | Levulan (Aminolevulinic Acid) | Raloxifene Hydrochloride |
| Cometriq (Cabozantinib-S-Malate) | Cytosar-U (Cytarabine) | Linfolizin (Chlorambucil) | Ramucirumab |
| CVP | Cytoxan (Cyclophosphamide) | LipoDox (Doxorubicin Hydrochloride Liposome) | Rasburicase |
| Cyclophosphamide | Dabrafenib | Lomustine | R-CHOP |
| Cyfos (Ifosfamide) | Dacarbazine | Lonsurf (Trifluridine and Tipiracil Hydrochloride) | R-CVP |
| Cyramza (Ramucirumab) | Dacogen (Decitabine) | Lupron (Leuprolide Acetate) | Recombinant Human Papillomavirus (HPV) Bivalent Vaccine |
| Cytarabine | Dactinomycin | Lupron Depot (Leuprolide Acetate) | Recombinant Human Papillomavirus (HPV) Nonavalent Vaccine |

TABLE 4-continued

| Cancer Therapeutic Agents | | | |
|---|---|---|---|
| Cytarabine Liposome | Daratumumab | Lupron Depot-Ped (Leuprolide Acetate) | Recombinant Human Papillomavirus (HPV) Quadrivalent Vaccine |
| Dasatinib | Darzalex (Daratumumab) | Lupron Depot-3 Month (Leuprolide Acetate) | Recombinant Interferon Alfa-2b |
| Daunorubicin Hydrochloride | Doxorubicin Hydrochloride Liposome | Lupron Depot-4 Month (Leuprolide Acetate) | Regorafenib |
| Decitabine | Dox-SL (Doxorubicin Hydrochloride Liposome) | Lynparza (Olaparib) | R-EPOCH |
| Defibrotide Sodium | DTIC-Dome (Dacarbazine) | Margibo (Vincristine Sulfate Liposome) | Revtimid (Lenalidomide) |
| Defitelio (Defibrotide Sodium) | Efudex (Fluorouracil--Topical) | Matulane (Procarbazine Hydrochloride) | Rheumatrex (Methotrexate) |
| Degarelix | Elitek (Rasburicase) | Mechlorethamine Hydrochloride | Rituxan (Rituximab) |
| Denileukin Diftitox | Ellence (Epirubicin Hydrochloride) | Megestrol Acetate | Rituximab |
| Denosumab | Elotuzumab | Mekinist (Trametinib) | Rolapitant Hydrochloride |
| DepoCyt (Cytarabine Liposome) | Eloxatin (Oxaliplatin) | Melphalan | Romidepsin |
| Dexamethasone | Eltrombopag Olamine | Melphalan Hydrochloride | Romiplostim |
| Dexrazoxane Hydrochloride | Emend (Aprepitant) | Mercaptopurine | Rubidomycin (Daunorubicin Hydrochloride) |
| Dinutuximab | Empliciti (Elotuzumab) | Mesna | Ruxolitinib Phosphate |
| Docetaxel | Enzalutamide | Mesnex (Mesna) | Sclerosol Intrapleural Aerosol (Talc) |
| Doxil (Doxorubicin Hydrochloride Liposome) | Epirubicin Hydrochloride | Methazolastone (Temozolomide) | Siltuximab |
| Doxorubicin Hydrochloride | EPOCH | Methotrexate | Sipuleucel-T |
| Erbitux (Cetuximab) | Everolimus | Methotrexate LPF (Methotrexate) | Somatuline Depot (Lanreotide Acetate) |
| Eribulin Mesylate | Evista (Raloxifene Hydrochloride) | Mexate (Methotrexate) | Sonidegib |
| Erivedge (Vismodegib) | Evomela (Melphalan Hydrochloride) | Mexate-AQ (Methotrexate) | Sorafenib Tosylate |
| Erlotinib Hydrochloride | Exemestane | Mitomycin C | Sprycel (Dasatinib) |
| Erwinaze (Asparaginase Erwinia chrysanthemi) | 5-FU (Fluorouracil Injection) | Mitoxantrone Hydrochloride | STANFORD V |
| Etopophos (Etoposide Phosphate) | 5-FU (Fluorouracil--Topical) | Mitozytrex (Mitomycin C) | Sterile Talc Powder (Talc) |
| Etoposide | Fareston (Toremifene) | MOPP | Sternalc (Talc) |
| Etoposide Phosphate | Farydak (Panobinostat) | Mozobil (Plerixafor) | Stivarga (Regorafenib) |
| Evacet (Doxorubicin Hydrochloride Liposome) | Faslodex (Fulvestrant) | Mustargen (Mechlorethamine Hydrochloride) | Sunitinib Malate |

TABLE 4-continued

| Cancer Therapeutic Agents | | | |
|---|---|---|---|
| FEC | Fluorouracil--Topical | Mutamycin (Mitomycin C) | Sutent (Sunitinib Malate) |
| Femara (Letrozole) | Flutamide | Myleran (Busulfan) | Sylatron (Peginterferon Alfa-2b) |
| Filgrastim | Folex (Methotrexate) | Mylosar (Azacitidine) | Sylvant (Siltuximab) |
| Fludara (Fludarabine Phosphate) | Folex PFS (Methotrexate) | Mylotarg (Gemtuzumab Ozogamicin) | Synovir (Thalidomide) |
| Fludarabine Phosphate | FOLFIRI | Nanoparticle Paclitaxel (Paclitaxel Albumin-stabilized Nanoparticle Formulation) | Synribo (Omacetaxine Mepesuccinate) |
| Fluoroplex (Fluorouracil--Topical) | FOLFIRI-BEVACIZUMAB | Navelbine (Vinorelbine Tartrate) | Tabloid (Thioguanine) |
| Fluorouracil Injection | FOLFIRI-CETUXIMAB | Necitumumab | TAC |
| FOLFIRINOX | Gazyva (Obinutuzumab) | Nelarabine | Tafinlar (Dabrafenib) |
| FOLFOX | Gefitinib | Neosar (Cyclophosphamide) | Tagrisso (Osimertinib) |
| Folotyn (Pralatrexate) | Gemcitabine Hydrochloride | Netupitant and Palonosetron Hydrochloride | Talc |
| FU-LV | GEMCITABINE-CISPLATIN | Neupogen (Filgrastim) | Talimogene Laherparepvec |
| Fulvestrant | GEMCITABINE-OXALIPLATIN | Nexavar (Sorafenib Tosylate) | Tamoxifen Citrate |
| Gardasil (Recombinant HPV Quadrivalent Vaccine) | Gemtuzumab Ozogamicin | Nilotinib | Tarabine PFS (Cytarabine) |
| Gardasil 9 (Recombinant HPV Nonavalent Vaccine) | Gemzar (Gemcitabine Hydrochloride) | Ninlaro (Ixazomib Citrate) | Tarceva (Erlotinib Hydrochloride) |
| Gilotrif (Afatinib Dimaleate) | Halaven (Eribulin Mesylate) | Nivolumab | Targretin (Bexarotene) |
| Gleevec (Imatinib Mesylate) | Herceptin (Trastuzumab) | Nolvadex (Tamoxifen Citrate) | Tasigna (Nilotinib) |
| Gliadel (Carmustine Implant) | HPV Bivalent Vaccine, Recombinant | Nplate (Romiplostim) | Taxol (Paclitaxel) |
| Gliadel wafer (Carmustine Implant) | HPV Nonavalent Vaccine, Recombinant | Obinutuzumab | Taxotere (Docetaxel) |
| Glucarpidase | HPV Quadrivalent Vaccine, Recombinant | Odomzo (Sonidegib) | Temodar (Temozolomide) |
| Goserelin Acetate | Hycamtin (Topotecan Hydrochloride) | OEPA | Temozolomide |
| Thioguanine | Hydrea (Hydroxyurea) | Ofatumumab | Temsirolimus |
| Thiotepa | Topotecan Hydrochloride | OFF | Thalidomide |
| Tolak (Fluorouracil--Topical) | Toremifene | Olaparib | Thalomid (Thalidomide) |
| Trabectedin Tipiracil | Trifluridine and (Temsirolimus) Hydrochloride | Torisel (Vinblastine Sulfate) | Velban |
| Trametinib | Trisenox (Arsenic Trioxide) | Tositumomab and Iodine I 131 Tositumomab | Velcade (Bortezomib) |
| Trastuzumab | Tykerb (Lapatinib Ditosylate) | Totect (Dexrazoxane Hydrochloride) | Velsar (Vinblastine Sulfate) |
| Treanda (Bendamustine Hydrochloride) | Unituxin (Dinutuximab) | TPF | Vandetanib |

TABLE 4-continued

Cancer Therapeutic Agents

| | | | |
|---|---|---|---|
| Vemurafenib | Uridine Triacetate | Vectibix (Panitumumab) | VAMP |
| Venclexta (Venetoclax) | VAC | VeIP | Vidaza (Azacitidine) |
| Venetoclax | Vorinostat | Vinorelbine Tartrate | Vinblastine Sulfate |
| Viadur (Leuprolide Acetate) | Votrient (Pazopanib Hydrochloride) | VIP | Vincasar PFS (Vincristine Sulfate) |
| Varubi (Rolapitant Hydrochloride) | Wellcovorin (Leucovorin Calcium) | Vismodegib | Vincristine Sulfate |
| XELIRI | Xalkori (Crizotinib) | Vistogard (Uridine Triacetate) | Vincristine Sulfate Liposome |
| XELOX (Capecitabine) | Xeloda (Glucarpidase) | Voraxaze 223 Dichloride) | Xofigo (Radium |
| Xgeva (Denosumab) | Xtandi (Enzalutamide) | Yervoy (Ipilimumab) | Yondelis (Trabectedin) |
| Zaltrap (Ziv-Aflibercept) | Zinecard (Dexrazoxane Hydrochloride) | Zoledronic Acid | Zykadia (Ceritinib) |
| Zarxio (Filgrastim) | Ziv-Aflibercept | Zolinza (Vorinostat) | Zytiga (Abiraterone Acetate) |
| Zelboraf (Vemurafenib) | Zofran (Ondansetron Hydrochloride) | Zometa (Zoledronic Acid) | |
| Zevalin (Ibritumomab Tiuxetan) | Zoladex (Goserelin Acetate) | Zydelig (Idelalisib) | |

Combination cancer therapeutic agents with an mTOR inhibitor offer many advantages. Drugs with different target sites or mechanisms of action are used together to enhance destruction of tumor cells. If the adverse effects of the component agents are different, the combination may be no more toxic than the individual agents given separately. Combinations that include a cycle-nonspecific drug administered first, followed by a phase-specific drug, may offer the advantage that cells surviving treatment with the first drug are provoked into mitosis and, therefore, are more susceptible to the second drug. Another advantage of combination therapy is the decreased possibility of development of drug resistance.

Special considerations associated with administration of cancer therapeutic agents include evaluation of the subject's quality of life, medical and nutritional support, control of pain, and psychologic comfort.

C. Administration

Where the compounds of the invention are administered in conjunction with other therapies, dosages of the co-administered compounds will of course vary depending on the type of co-drug employed, on the specific drug employed, on the condition being treated and so forth.

Accordingly, an mTOR inhibitor, e.g., an mTOR inhibitor described herein, may be used at low, immune enhancing, dose in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

An mTOR inhibitor, e.g., an mTOR inhibitor described herein, at a preferred dose, and the at least one additional therapeutic agent (e.g., a second mTOR inhibitor, a second antiretroviral agent, or a cancer therapeutic agent) can be administered simultaneously, in the same or in separate compositions, or sequentially. For sequential administration, the mTOR inhibitor can be administered first, and the additional agent can be administered second, or the order of administration can be reversed. In some embodiments, the mTOR inhibitor is administered as a pretreatment, e.g., 1 week, 2 weeks, 3 weeks, 4 weeks, 5 weeks, 6 weeks, 7 weeks, 8 weeks, 9 weeks, 10 weeks, 11 weeks, 12 weeks or more, before treatment with the at least one additional therapeutic agent.

INK128 may be administered alone, or in combination in a therapeutically effective amount from about 0.5 mg to about 4 mg to achieve a plasma concentration of about 200 nM in the subject. The mTOR inhibitor, Torin-2 may be administered in a therapeutically effective amount from about 0.05 mg to about 10 mg. GSK2126458 may be administered in a therapeutically effective amount from about 0.04 mg to about 0.25 mg. In other embodiments, AZD2014 may be administered in a therapeutically effective amount from about 5 mg to about 50 mg.

In some embodiments, an mTOR inhibitor, e.g., an mTOR inhibitor described herein, is administered to a HIV-infected subject who also has cancer, e.g., a cancer described herein. The subject may receive treatment with an additional therapeutic agent.

A dose of an mTOR inhibitor, can allow for more aggressive administration of the additional treatment. Thus, in an embodiment, the unit dosage, total dosage, frequency of administration, or number of administrations, is increased. In an embodiment, the increase is relative to a reference administration, e.g., the standard of care that is provided in the absence of a low, immune enhancing, dose of mTOR inhibitor. In an embodiment, the increase is relative to an administration that would give the maximum tolerable or acceptable levels of immune suppression, in the absence of a low, immune enhancing, dose of mTOR inhibitor. In another embodiment, the immune enhancing dose of an mTOR inhibitor, can allow for less aggressive administration of the additional treatment. Thus, in an embodiment, the unit dosage, total dosage, frequency of administration, or number of administrations, is decreased. In an embodiment, the decrease is relative to a reference administration, e.g., the standard of care that is provided in the absence of a low, immune enhancing, dose of mTOR inhibitor. In an embodiment, the decrease is relative to an administration that would give the maximum tolerable or acceptable levels of immune suppression, in the absence of a low, immune enhancing, dose of mTOR inhibitor.

In some embodiments, an antiretroviral agent as described herein, is administered to a HIV-infected subject who also has cancer, e.g., a cancer described herein. The subject may receive treatment with an additional therapeutic agent. Thus, antiretroviral agents could include the following at daily doses:

| Integrase inhibitors (daily doses) |
| --- |
| Raltegravir (400-800 mg) |
| Elvitegravir (85-150 mg) |
| Dolutegravir (50-100 mg) |
| Reverse transcriptase inhibitors (daily doses) |
| Lamivudine (150-300 mg) |
| Abacavir (600 mg) |
| Emtricitabine (200 mg) |
| Tenofovir (300 mg) |
| Efavirenz (600 mg) |
| Nevirapine (200-400 mg) |
| Etravirine (400 mg) |
| Rilpivirine (25 mg) |
| Protease inhibitors (daily doses) |
| Indinavir (1200-2400 mg) |
| Atazanavir (150-300 mg) |
| Darunavir (800-1200 mg) |
| CCR5 antagonists (daily doses) |
| Maraviroc (150-600 mg) |

Dosing strategies for anticancer drugs are known in the art and can be found in Physicians Desk Reference and other references such as "Dosing strategies for anticancer drugs: the good, the bad and body-surface area," A Felici, J Verweij, A Sparreboom—European Journal of Cancer, 2002. For example, AZD2014 has been administered orally to solid tumor cancer patients in single doses up to 100 mg and multiple doses up to 100 mg twice daily (BID). In other examples, patients receiving oral GSK458 once or twice daily in a dose escalation design to define the maximally tolerated dose (MTD). Expansion cohorts evaluated pharmacodynamics (PD), pharmacokinetics (PK), and clinical activity in histologically- and molecularly-defined cohorts. 170 patients received doses ranging from 0.1 to 3 mg once or twice daily. See, Munster P., et al., "First-in-Human Phase I Study of GSK2126458, an Oral Pan-Class I Phosphatidylinositol-3-Kinase Inhibitor, in Patients with Advanced Solid Tumor Malignancies," *Clin Cancer Res.* 2016 Apr. 15; 22(8):1932-9. doi: 10.1158/1078-0432.CCR-15-1665. Epub 2015 Nov. 24.

Dosing is dependent on severity and responsiveness of the condition to be treated, with course of treatment lasting from several days to several months or until a reduction in HIV viral titre (routinely measured by Western blot, ELISA, RT-PCR, or RNA (Northern) blot) is effected or a diminution of disease state is achieved. Optimal dosing schedules are easily calculated from measurements of drug accumulation in the body. Persons of ordinary skill can easily determine optimum dosages, dosing methodologies, and repetition rates. Therapeutically or prophylactically effective amounts (dosages) may vary depending on the relative potency of individual compositions, and can generally be routinely calculated based on molecular weight and EC50s in in vitro and/or animal studies. For example, given the molecular weight of drug compound (derived from sequence and chemical structure) and an experimentally derived effective dose such as an $IC_{50}$, for example, a dose in mg/kg is routinely calculated. In general, dosage is from 0.001 μg to 100 g and may be administered once or several times daily, weekly, monthly, yearly, or even every decade.

D. Routes of Administration

In some embodiments, an mTOR inhibitor, alone or in combination with a therapeutic agent is administered orally, intravenously, intramuscularly, intrathecally, subcutaneously, sublingually, buccally, rectally, vaginally, by ocular route or by otic route, nasally, by inhalation, by nebulization, cutaneously, topically, or systemically, and transdermally. Preferable administration may be parenterally. Parenteral vehicles include sodium chloride solution, Ringer's dextrose, dextrose and sodium chloride, lactated Ringer's or fixed oils and other vehicle known to one of skill in the art. Intravenous vehicles may include fluid and nutrient replenishers, electrolyte replenishers (such as those based on Ringer's dextrose). In some embodiments, an mTOR inhibitor, for parenteral administration may be in the form of a sterile injectable preparation, such as a sterile injectable aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1, 3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the mTOR inhibitors in combination with a therapeutic agent is provided as a liquid suspension or as a freeze-dried product. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

In certain embodiments, the mTOR inhibitors in combination with a therapeutic agent may be provided in the form of a solution, suspension and gel. In other embodiments, formulation of the conjugate vaccine may contain a major amount of water that may be purified in addition to the active ingredient. Minor amounts of other ingredients such as pH adjusters, emulsifiers, dispersing agents, buffering agents, preservatives, wetting agents, jelling agents, colors, and the like can also be present.

Compositions comprising mTOR inhibitors, may be administered in a number of ways either alone or in combination with other treatments, at the same time, at different times, either simultaneously or sequentially depending on the condition to be treated and whether local or systemic treatment is desired. Administration may be by direct injection, or by intrathecal injection, or intravenously, or by stereotaxic injection. The route of administration can be selected based on the disease or condition, the effect desired, and the nature of the cells being used. Actual methods of preparing dosage forms are known, or will be apparent, to those skilled in the art. (See Remington: The Science and Practice of Pharmacy, 22nd edition, 2012, Pharmaceutical Press.) Where a composition as described herein is to be administered to an individual, administration is preferably in a "prophylactically effective amount" or a "therapeutically effective amount," this being sufficient to show benefit to the individual.

The number of administrations can vary. Alternatively, administration may be, for example, daily, weekly, or monthly. The actual amount administered, and rate and time-course of administration, will depend on the age, sex, weight, of the subject, the stage of the disease, and severity of what is being treated (including prophylactic treatment). Prescription of treatment, e.g., decisions on dosage is within the responsibility of general practitioners and other medical doctors.

Effective clinical use of use cancer therapeutic agents depends on the ability to balance the killing of tumor cells against the inherent toxicity of many of these drugs to host cells. Because of the narrow therapeutic indices of cancer therapeutic agents, dosages are frequently calculated based on body surface area (BSA) rather than body mass. Correlation is better between body weight and these toxicities. Cancer therapeutic agents can be administered by intraperitoneal, transdermal, intratumor injection, IV, SC, IM, topical, intracavitary, intralesional, intravesicular, intrathecal, or intra-arterial routes. The route chosen depends on the individual agent and is determined by drug toxicity; location, size, and type of tumor; and physical constraints.

Cancer therapeutic agents are commonly administered in various combinations of dosages and timing; the specific regimen is referred to as a protocol. A protocol may use one or as many as five or six different antineoplastic agents. Selection of an appropriate protocol should be based on type of tumor, grade or degree of malignancy, stage of the disease, condition of the animal, and financial considerations. Preferences of individual clinicians for treatment of specific neoplastic conditions may also vary. Regardless of the protocol chosen, a thorough knowledge of the mechanism of action and toxicities of each therapeutic agent is essential.

4. SUMMARY OF EXPERIMENTAL RESULTS

The following is a summary of results of experiments described in the Examples of this application:
- INK128 inhibits R5 and X4 HIV replication in primary cells;
- INK128 inhibits entry of R5, but not X4, HIV in primary cells;
- INK128 inhibits HIV gene expression;
- INK128 has favorable drug interactions with current antiretroviral classes;
- INK128 inhibits HIV replication in vivo;
- Torin-2 inhibits HIV in vitro in the absence of cell toxicity; and
- INK128 inhibits tumor growth in NSG mice.

5. EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

Cell Proliferation and Infectivity Assays

PBLs were isolated from buffy coats of HIV seronegative donors (New York Blood Center). The laboratory-adapted strains HIV BaL and HIV HXB2; primary isolates HIV 92BR020, 92UG031, 93BR029, and 93UG082; and multi-drug resistant molecular clone NL4329129-2 were obtained from the NIH AIDS Repository. Primary isolate 2044 was from Paul Clapham (Windeyer Institute), and 1633 and 1638 from the Institute of Human Virology (University of Maryland School of Medicine). Maraviroc, efavirenz, raltegravir, and indinavir were from the NIH AIDS Repository. INK128 was purchased from ApexBio. Proliferation of PBLs was measured by the MTT kit (Roche), following the manufacturer's directions. PBL infectivity assays were performed as described herein.

Cell Fusion Assay

CD4 cells were isolated from PBL cultures maintained for 7 days in the presence of different concentrations of INK128. Isolation of CD4 cells was done by positive selection using immunomagnetic beads following the manufacturer's directions (Invitrogen™). Cell fusion was analyzed by measuring cytoplasmic dye exchange between fluorescent dye-labeled CD4 lymphocytes (targets) and transfected 293T cells expressing the R5 HIV Env or X4 HIV Env (effectors) using flow cytometry analysis. This methodology is described in detail herein.

Quantitation of CD4, CCR5, and CXCR4

Quantitation of CCR5, CXCR4, and CD4 was done as described (59) using the following antibody clones: clone 45531 (CCR5), clone 12G5 (CXCR4), and clone RPA-T4 (CD4). For CCR5 and CXCR4, lymphocytes were first gated on CD3 (clone UCHT1) and CD4 (clone RPA-T4). For CD4, lymphocytes were gated using CD3 (clone UCHT1) in combination with CD8 (clone SK1). All antibodies were from BD Biosciences except for the CCR5 antibody, which was from R&D Systems. The methodology is fully described herein.

Real-Time PCR for Detection of Early Products of Reverse Transcription and of Integrated HIV DNA Activated PBLs were infected with R5 and X4 HIV strains using a MOI of 0.01. Infected cells were cultured in the presence of IL-2 and different concentrations of INK128. Cell aliquots were collected at 16 and 72 hours for analyses of early products of reverse transcription and of integration, respectively, by real time PCR. Detection of early products of reverse transcription was done with primers specific for the R/U5 region (60). For detection of integrated HIV DNA, a real-time nested Alu-HIV PCR assay was used as previously described (61, 62), with the modifications described herein.

DNA was isolated using Miniblood kit (Qiagen™). PCR amplification was performed using Quantitect SYBR Green™ PCR Kit (Qiagen™) in a LightCycler™ (Biorad™). Detection of early products of reverse transcription was done in reactions containing 100 ng of DNA and the primer pair 5'-GCTCTCTGGCTAACTAGGGAAC-3' (SEQ ID NO. 1) and 5'-TGACTAAAAGGGTCTGAGGGAT-3' (SEQ ID NO. 2) (R/U5 region) (60). Samples were also amplified with primers for the housekeeping gene α-tubulin. Both sets of PCR reactions were done at an annealing temperature of 56° C. Amplified products were analyzed by denaturation/renaturation to verify the specific Tm. The PCR cycle at which the signal entered the exponential range was used for quantification, and HIV copy numbers were corrected for those of α-tubulin. Standard curves for HIV and α-tubulin copy numbers were generated by analyzing serial dilutions of plasmids carrying the corresponding sequences. For detection of integrated HIV DNA, we used a real-time nested Alu-HIV PCR assay previously described (61, 62), with the following modifications. The first PCR used 100 ng of DNA template and primers Alu (5'-GCCTCCCAAAGTGCTGGGATTACAG-3') SEQ ID NO. 3 and Gag (5'-GCTCTCGCACCCATCTCTCTCC-3') (SEQ ID NO. 4) for 25 cycles. From this reaction, ¹⁄₂₀ of amplified product was used as template for the nested PCR with primers LTR-R (5'-GCCTCAATAAAGCTTGCCTTGA-3') (SEQ ID NO. 5) and LTR-U5 (5'-TCCACACTGACTAAAAGGGTCTGA-3') (SEQ ID NO. 6), as described (61, 62) except for the annealing temperature, which was 61° C. in our reactions. As a standard curve for relative quantification of integrated DNA, the Alu-gag was first run using serial dilutions of DNA isolated from HIV infected PBLs (diluted in HIV-negative DNA).

CD4 cells were isolated from PBL cultures maintained for 7 days in the presence of different concentrations of INK128. Isolation of CD4 cells was done by positive selection using immunomagnetic beads (Invitrogen™) following the manufacturer's directions. HIV JRFL-Env (R5) and HXB2-Env (X4) expressing 293T cells were prepared by calcium phosphate transfection, using 5 μg of Env-expressing plasmid and 2.5 μg of cRev plasmid per 60-mm dish. CD4 lymphocytes (targets) were labeled with calcein acetoxymethyl ester (Calcein AM), and HIV Env-expressing 293T cells (effector cells) were labeled with orange dye, 5- and 6-(4-chloromethyl)benzoyll-amino) tetramethylrhodamine (CMTMR) on day 2 after transfection. Calcein AM and CMTMR dyes (both from Invitrogen) were used at final concentrations of 75 nM and 1 μM, respectively. Target cells (1×105) and effector cells (3×105) were cocultured in triplicate wells of a 96-well plate in Hepes-buffered DMEM (pH 7.2) supplemented with 1 mg/mL BSA (Sigma) for 2.5 h at 37° C. to allow fusion. INK128 was added at different concentrations at the beginning of the 2.5-h incubation. Cells were washed with PBS, and incubated with Trypsin/EDTA for 5 min at 37° C. to stop the fusion reaction and to disrupt cell clusters. Trypsin was neutralized by adding DMEM containing 10% (vol/vol) FBS and cells were washed with PBS. Cells were then analyzed on a FACSCalibur™ (BD Biosciences™) after collecting 40,000 events from each well using Cellquest™ software (BD Biosciences™). Fusion was scored as a number of cells positive for both dyes in the histogram. The results (fusion events) were normalized for the total number of target cells in the histogram. Background was determined by analyzing fusion in the presence of the fusion inhibitor, C34 peptide at 1 μM, a concentration that abrogates fusion. The obtained background signal (false positive fusion events) was subtracted from the signal obtained in the absence of C34. Quantification of CD4, CCR5, and CXCR4. Before staining, PBLs were washed twice with PBS and incubated in blocking buffer (PBS containing 2% human serum, 5% horse serum, and 0.1% sodium azide) for 30 min at room temperature. Cells were then stained with the antibodies for 30 min at room temperature, washed twice with PBS, and acquired on a FACS Calibur™ (BD Biosciences™) using Cellquest™ software (BD Biosciences) Immunofluorescence intensity was measured as an estimate of the average number of molecules on the cell surface. Fluorescence was measured using the Quantiquest™ system (BD Biosciences™), which produces a regression line from a series of Quantibrite-phycoerythrin (PE)™ bead standards (BD Biosciences™). The mean number of surface molecules for a cell labeled with a PE antibody was then determined from the FL-2 value of the cell using this linear regression and taking into account the PE/antibody ratio for each antibody (1:1 in our reagents).

Semiquantitative RT-PCR for Detection of Cellular HIV mRNA

Total cellular RNA was isolated using the Qiagen™ RNA Isolation Kit (Qiagen™) RNA was then treated with DNase I, Amplification Grade (Invitrogen™), and reverse transcribed with SuperScript III First-Strand Synthesis Supermix™ (Invitrogen™) using hexamer primers. An aliquot of the cDNA was used as a template for PCR amplification of full length, unspliced HIV cDNA using primers US.1a and US.2a, and another aliquot for amplification with primer pairs specific for housekeeping [beta]-actin sequences (63).

Generation of Humanized Mice, Quantitation of Plasma HIV RNA and Lymphocyte Subsets Animal protocols were approved by the Institutional Animal Care and Use Committee, University of Maryland School of Medicine. NSG mice (5-7 weeks) were intraperitoneally (i.p) injected with 107 PBLs isolated from buffy coats of healthy donors. Three weeks later mice were screened for human lymphocytes in peripheral blood samples. Successfully reconstituted animals were i.p injected with 15,000 units of 50% tissue culture infective dose (TCID50) of HIV BaL, followed by daily i.p. treatment with INK128 [1-5 mg/kg/day, prepared in a 1-methyl-2-pyrrolidinone (NMP)/polyvinylpyrrolidone k30 (PVP) solution as described (26)] or PBS (in NMP/PVP solution) for 14 days. Animals were monitored daily for external signs of clinical deterioration. Blood samples, drawn from the retroorbital vein on days 7 and 14 after infection, were analyzed for plasma HIV RNA copy number by quantitative RT PCR using HIV gag primers (64) and for human CD4/CD8 ratios (flow cytometry analysis).

MTT Assays

Cell proliferation was measured by a colorimetric MTT test (Roche™). This test is based on the reduction of the yellow colored MTT [3-(4,5-dimethylthiazol-2-yl)-2,5-diphenyltetrazolium bromide] to blue formazan by mitochondrial dehydrogenases. The quantity of formazan produced (absorbance at 490 nm) is directly proportional to the number of living cells. Briefly, cell aliquots were seeded in 96-well plates (100 µL) and incubated with 10 µL of MTT solution for 4 hours at 37° C. A solubilization solution (50 µL) was added and plates incubated overnight at 37° C. MTT conversion to formazan by mitochondrial dehydrogenase was assayed by optical density at 490 nm measured in an ELISA plate reader.

Infectivity Assays

PBLs were separated from buffy coats by density centrifugation over Ficoll-Hypaque (Sigma™), and activated by culture in the presence of 1 µg/mL anti-human CD3 antibody (clone x35, Fisher Scientific™) and 2 µg/mL anti-human CD28 antibody (Clone CD28.6, eBioscience™) for 3 days. Activated cells were infected by incubation with virus at a multiplicity of infection (MOI) of 0.001 for 2 hours. Infected cells were washed three times with PBS and cultured in 5% CO2 at 37° C., in RPMI/10% FBS supplemented with 100 units/mL IL-2 (Roche™) and antiviral drugs, in 96-well flat-bottom plates at a density of 2×105 PBLs per 200 µL. Following 3 d of culture, half of the medium was replaced with fresh medium containing IL-2 and antiviral drugs. On day 7, viral replication was measured by p24 ELISA (Coulter) in culture supernatants and cell viability was measured by MTT assays.

Quantification of Plasma HIV RNA

For quantification of HIV RNA, viral RNA was extracted from 40 µL of plasma samples using Qiagen viral RNA Minikit™ (Qiagen™). RNA was converted to cDNA using SuperScript III Supermix™ (Invitrogen™). cDNA was amplified with HIV gag consensus primers (64), using Quantitec™ SYBR Green PCR kit (Qiagen™) in a LightCycler™ (BioRad™). Reactions were heated at 50° C. for 2 minutes, 95° C. for 15 seconds, followed by 35 amplification cycles (94° C. for 15 seconds, 58° C. for 30 seconds, 72° C. for 30 seconds). A standard curve was prepared by serial dilutions of RNA extracted from plasma of an HIV patient with known HIV RNA copy number (HIV VQA RNA Quantification Standard; NIH AIDS Repository, catalog no. 3443). Peripheral blood CD4/CD8 ratios were determined by staining of whole blood with FITC-conjugated mouse anti-CD4 and APC-conjugated mouse anti-CD8 monoclonal antibodies (BD Pharmingen™), followed by flow cytometry analysis.

Statistics Analyses

EC50 values were determined by variable slope nonlinear regression analysis. Unpaired two-tailed t tests were used to check for statistical significant differences between INK128 EC50 values of R5 HIV versus X4 HIV in infectivity assays. Nonparametric Mann-Whitney tests were used to compare each treatment group and control group in animal studies. Statistical analyses were performed using GraphPad Prism™ (version 4.0). P<0.05 was considered significant.

Example 2: INK128 Inhibits R5 and X4 HIV Replication in Primary Cells

Figure 1B:
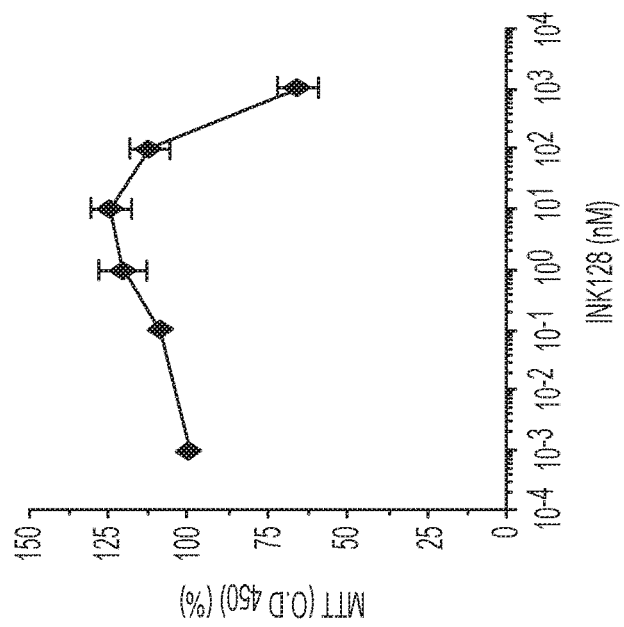
Figure 1A:
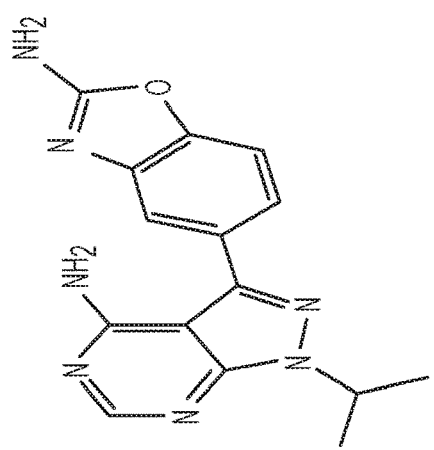

The chemical structure of INK128 is shown in FIG. 1A. The effect of INK128 was evaluated on proliferation of peripheral blood lymphocytes (PBLs) from four different donors. For each donor, PBLs were activated by treatment with anti-CD3/CD28 antibodies for 3 days, cultured in the presence of IL-2 and various dilutions of INK128 for 5 days, followed by measurement of cell proliferation by 3-(4,5-dimethylthiazol-2-yl)-2,5-diphenyl tetrazolium bromide (MTT) assays (FIG. 1B). INK128 did not inhibit cell proliferation at concentrations of up to 100 nM. Therefore, 100 nM was selected as the highest INK128 concentration in subsequent experiments evaluating antiviral activity.

The antiviral activity of INK128 was investigated in PBLs infected with CCR5 (R5)-tropic and CXCR4 (X4)-tropic HIV reference strains BaL and HXB2, respectively. In experiments with PBLs from three donors, INK128 inhibited replication of both viruses, but it inhibited BaL more potently than HXB2 (EC50s of 10.5 vs.38 nM; P=0.007 by two-tailed, unpaired t test) (FIG. 1C). Similarly, in primary isolates evaluated in three donors, INK128 was more potent against R5 (EC50s ranging 2.9-10.1 nM) than against X4 (EC50s ranging 17.5-36.7 nM) (Table 6).

TABLE 6

Activity of INK128 against primary isolates of HIV-1 in PBMCs

| Primary Isolate | Coreceptor tropism | Geometric mean INK128 EC50, nM (95% CI)* |
|---|---|---|
| HIV-1 93BR029 | R5 | 4.73 (2.78-8.05) |
| HIV-1 92UG031 | R5 | 10.15 (3.73-27.60) |
| HIV-1 93UG082 | R5 | 2.89 (0.82-10.13) |
| HIV-1 92BR020 | R5 | 1.03 (0.48-2.19) |
| HIV-1 2044 | X4 | 36.72 (13.38-100.8) |
| HIV-1 1633 | X4 | 17.47 (6.89-44.24) |
| HIV-1 1638 | X4 | 21.20 (3.25-138.4) |

*EC50 values were determined by variable slope nonlinear regression analysis using Graph Pad Prism software.
Data are from three experiments, each with a different donor.

Figure 2A:
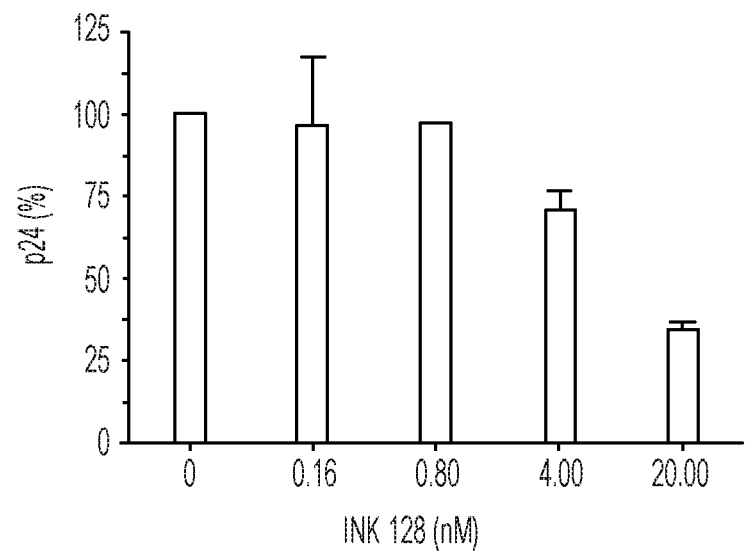
FIG. 2A-2B are bar graphs that illustrate how INK128 inhibits replication of multidrug resistant HIV molecular clone NL4329129-2. Activated PBLs were infected for 2 hours using a MOI of 0.001. Infected cells were cultured in IL-2 medium and the indicated concentrations of INK128. On day 7, virus production was measured by p24 ELISA in the culture supernatants (FIG. 2A), and cell viability was measured by MTT (FIG. 2B) according to an embodiment.
Figure 2B:
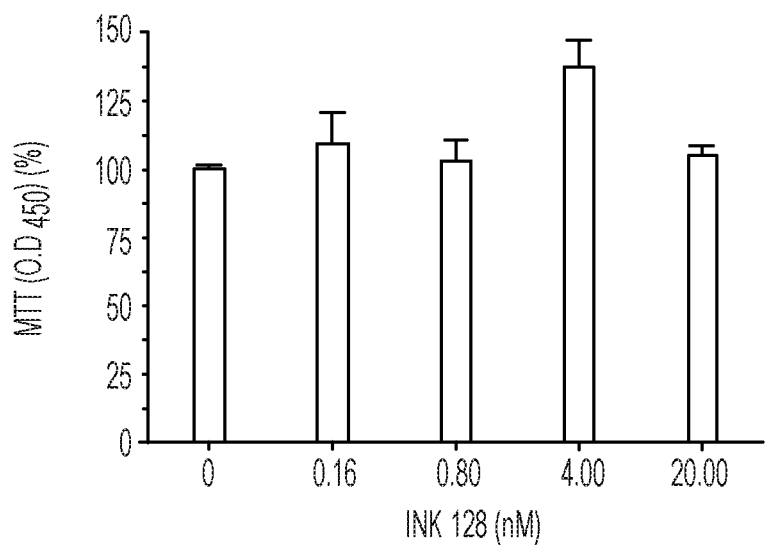

EC50 values were determined by variable slope nonlinear regression analysis. The difference in INK128 potency against R5 vs. X4 primary isolates was again significant (P=0.01 by two-tailed, unpaired t test). In addition, INK128 inhibited a multidrug-resistant HIV molecular clone NL4329129-2, which carries the RT gene amplified from plasma of a patient with multidrug resistant HIV (28), with an EC50 of 10.9 nM (FIG. 2A-2B). Together, these data show that INK128 inhibits replication of R5 and X4 strains of HIV, both laboratory adapted and primary isolates, in PBLs.

Example 3: INK128 Inhibits Entry of R5, but not X4, HIV in Primary Lymphocytes

Figure 3A:
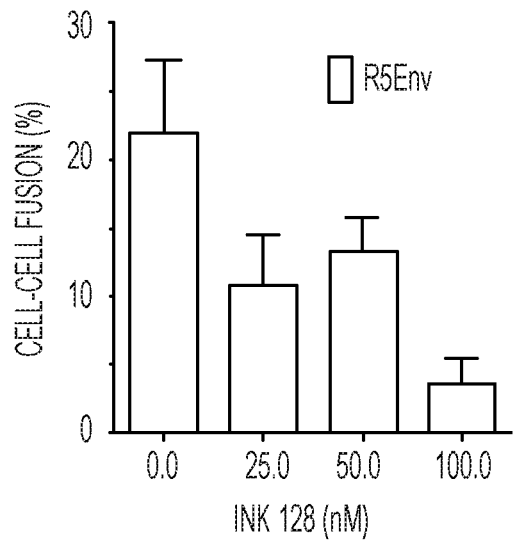
FIG. 3A-3F are graphs that illustrate that INK128 inhibits entry of R5, but not X4, HIV in primary lymphocytes.
Figure 3B:
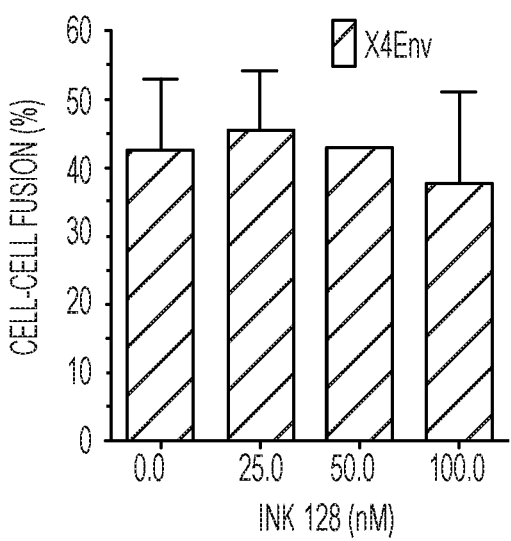
Figure 3C:
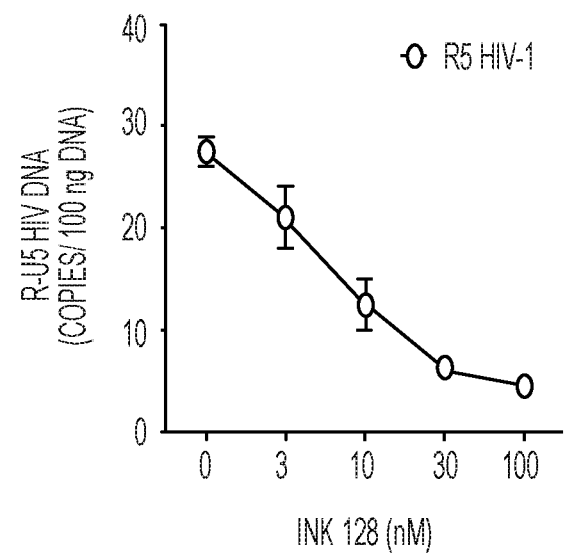
Figure 3D:
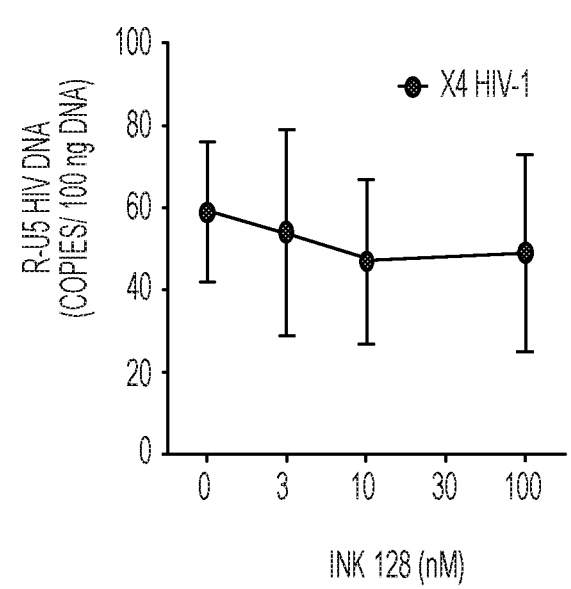
Figure 3E:
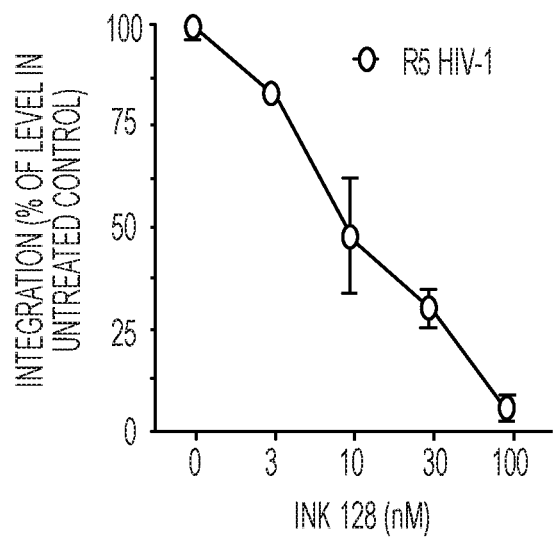
Figure 3F:
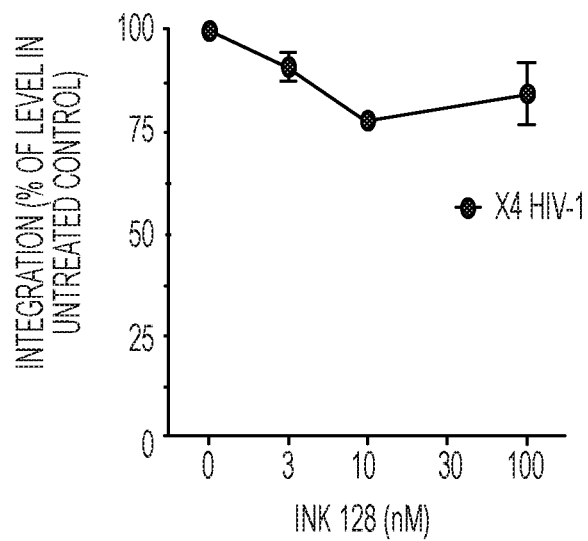

The mechanism of INK128 inhibition of HIV was evaluated. Because INK128 activity was more potent against R5 than against X4 HIV, it was hypothesized that INK128 affects entry of these viruses differently. To test this, cell-cell fusion assays were performed between 293T cells expressing R5 or X4 HIV envelopes (effectors) and INK128-treated primary CD4+ T cells (targets). In this assay, targets are labeled with the fluorescent dye calcein (green) and effectors with CMTMR (red) before co-culture. Fused cells score positive for both dyes. INK128 inhibited fusion of CD4+T target cells with R5 HIV JRFL Env, but not with X4 HIV HXB2 Env (FIG. 3A). These data, obtained with CD4 targets from two different donors, suggested inhibition at an early step of the R5, but not X4, HIV lifecycle. Downstream steps in HIV infection were evaluated by measuring early products of reverse transcription and integrated provirus using real-time PCR in PBLs from two donors. As expected from the cell-cell fusion data, PBLs infected with R5 HIV (JRFL) and treated with INK128 had decreased levels of early products of reverse transcription (R/U5 transcripts) (FIG. 3B) and integrated provirus (FIG. 3C).

In contrast, INK128 did not decrease R/U5 transcripts or integrated provirus on infection with X4 HIV (HXB2). Together these data demonstrate that INK128 inhibits entry of R5 HIV, but it does not inhibit X4 HIV infection before, or at the level of, integration. To gain insight into the mechanism of INK128 inhibition of R5 HIV entry, we evaluated the effects of INK128 on the receptor CD4 and the coreceptors CCR5 and CXCR4 by flow cytometry analysis in PBLs from three donors. In these experiments PBLs were stimulated with IL-2 alone (without previous activation with anti-CD3/CD28), in the presence and absence of INK128, for 7 days. INK128 reduced percentages of CCR5 expressing cells in both the CD4+ and CD8+ subsets of T cells (FIG. 4A). INK128 also decreased CCR5 receptor density (molecules/cell). In contrast, INK128 did not change CXCR4 levels, either in terms of percentage or density (FIG. 4B). In addition, INK128 did not impact CD4 receptor levels (FIG. 4C). Together, these data suggest that INK128 inhibits R5 HIV entry by decreasing CCR5 levels, consistent with the observation that CCR5 levels are limiting for R5 HIV infection (29-32).

Example 4: INK128 Inhibits HIV Gene Expression

Figures 5A, 5B, 5C:
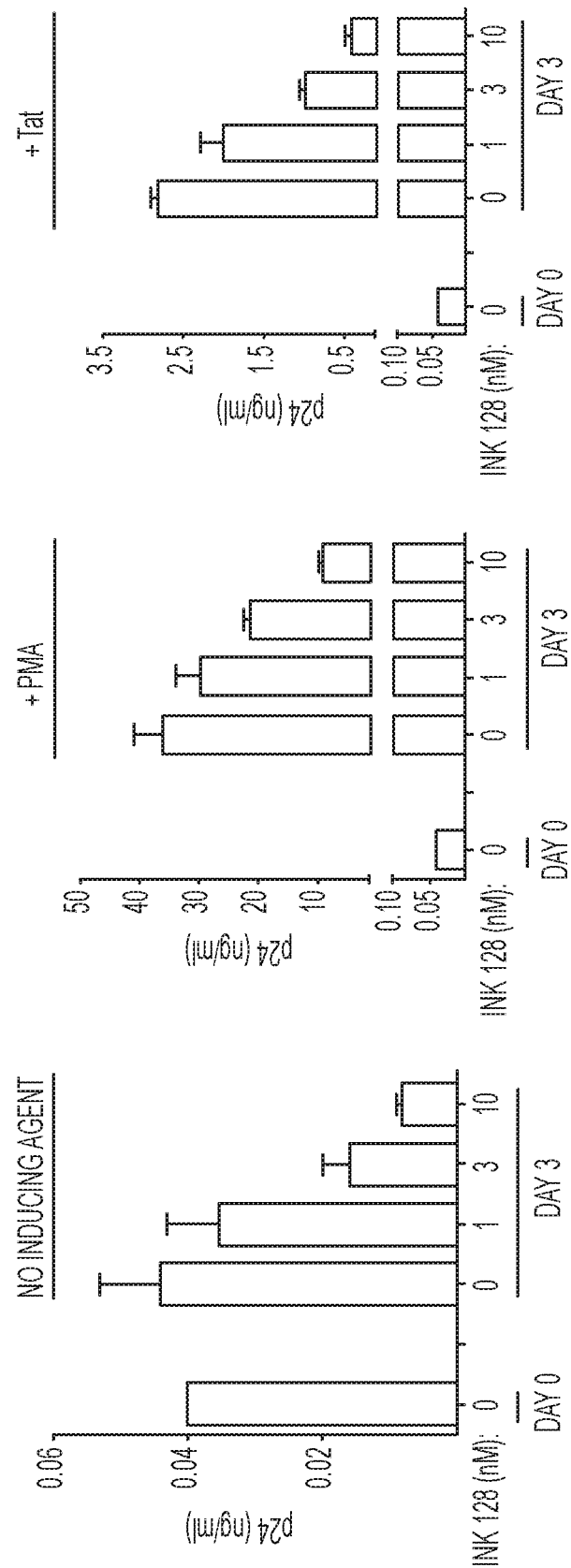
FIG. 5A-5C are bar graphs that illustrate INK128's inhibition of HIV activation in chronically infected cells. Latently HIV infected U1 cells were cultured in the presence of various concentrations of INK128 for 1 hour. Cultures were then untreated (FIG. 5A), or treated with HIV inducers PMA (FIG. 5B) and Tat protein (FIG. 5C). HIV production was measured by p24 ELISA in the culture supernatants on day 3 according to an embodiment.
Figure 6:
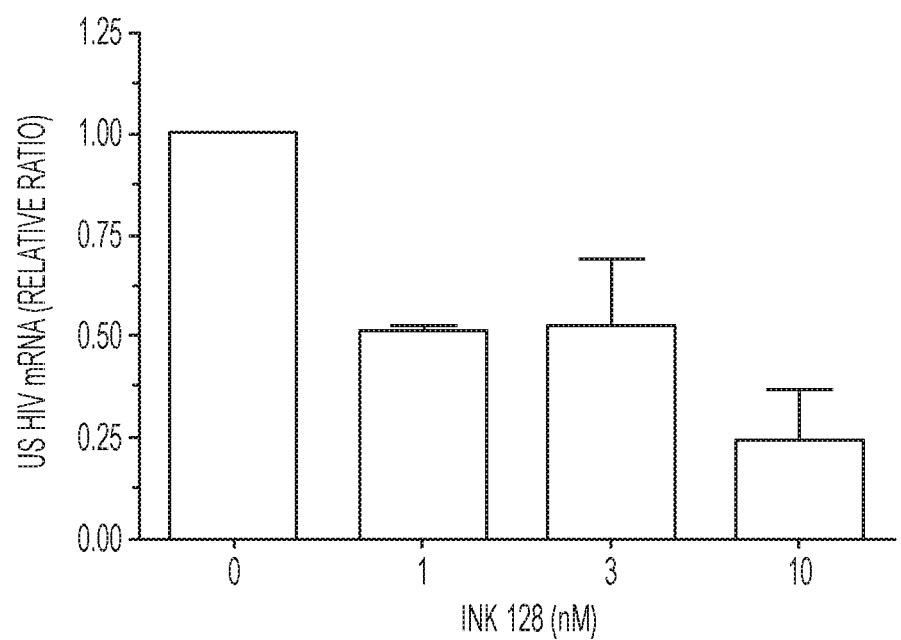
FIG. 6 is a bar graph that depicts how INK128 inhibits HIV transcription in U1 cells. U1 cells were cultured in the presence of 10 nM PMA and the indicated concentrations of INK128. After 2 days, cells were collected, mRNA isolated, quantified, reverse transcribed and amplified by real time PCR using unspliced HIV cDNA primer pair US.1a/US.2a and housekeeping [beta]-actin primers. For quantification, standard curves for unspliced HIV cDNA and [beta]-actin sequences were generated by performing 10-fold serial dilutions of mRNA isolated from PBLs acutely infected with HIV BaL. PCR amplification was performed using Quantitect® SYBR Green PCR Kit in a LightCycler®. Negative controls consisted of mixture reactions without the reverse transcription step according to an embodiment.

The effects of INK128 on activation of HIV in the chronically HIV-infected U1 cell line were examined. The U1 cell line carries two copies of the HIV provirus per cell (33). Under basal conditions, U1 cells express low levels of HIV, but HIV expression is enhanced by stimulation with the phorbol ester PMA or by exogenous addition of Tat (34, 35). U1 cells were cultured in the presence of INK128 in the absence and presence of 10 nM PMA or 1 µg/mL Tat. INK128 was used at concentrations <10 nM because optimization experiments showed inhibition of cell proliferation at higher concentrations, consistent with the increased drug sensitivity of U937 cells (parent cell line of U1) to TOR-KIs compared with primary cells (36). As expected, unstimulated U1 cells produced low levels of HIV p24, but production was increased by addition of PMA or Tat. INK128 inhibited p24 production in untreated cells as well as in cells treated with PMA or Tat (FIG. 5A-5C). RT-PCR analyses showed that INK128 inhibits synthesis of full-length unspliced HIV mRNA (FIG. 6). Together, these data suggest that INK128 inhibits transcription, both basal and induced, of the HIV LTR.

Example 5: INK128 has Favorable Drug Interactions with Current Antiretroviral Classes Available ARTs target the HIV lifecycle steps of entry, reverse transcription, integration, and maturation. The observation that INK128 reduces CCR5 density and inhibits R5 HIV entry suggested that INK128 could enhance the antiviral activity of the CCR5 antagonist Maraviroc. In addition, by targeting virus transcription, INK128 could have favorable interactions with inhibitors of reverse transcription (RTIs), integration (IIs), and protease (PIs). We therefore evaluated the antiviral potency of each ART class in the presence and absence of INK128. We conducted these assays in activated PBLs infected with R5 HIV BaL and treated with various dilutions of Maraviroc (CCR5 antagonist), Efavirenz (RTI), Raltegravir (II), and Indinavir (PI). INK128 was used at low concentrations (<EC50) to better detect changes in ART potency (Table 7).

TABLE 7

Fifty percent effective concentrations (EC50) of Maraviroc (MVC), Efavirenz (EFV), Raltegravir (RAL), and Indinavir (IND) against HIV-1 BaL, in the absence and presence of INK128 in PBMCs

| Treatment | MVC $EC_{50}$,$^a$ (95% CI) | EFV $EC_{50}$,$^a$ (95% CI) | RAL $EC_{50}$,$^a$ (95% CI) | IND $EC_{50}$,$^a$ (95% CI) |
|---|---|---|---|---|
| No INK128 | 1.78 nM (0.67-4.76) | 0.52 nM (0.31-0.87) | 0.65 nM (0.34-1.13) | 3.84 nM (3.21-4.57) |
| +3 nM INK128 | 0.54 nM (0.20-1.50) | 0.51 nM (0.34-0.75) | 0.81 nM (0.49-1.14) | 3.14 nM (2.31-4.27) |
| +10 nM INK128 | 0.30 nM (0.20-0.45) | 0.51 nM (0.33-0.78) | 0.57 nM (0.24-1.34) | 3 nM (1.10-8.18) |

$^a EC_{50}$ values are Geometric Means, determined by variable slope non-linear regression analysis using GraphPad Prism software. Data are from 2 experiments, each with a different donor.

In experiments with two donors, INK128 enhanced the antiviral potency of Maraviroc by five- to six fold, and had no negative effect on the potency of the other tested ARTs. Together, these data suggest that INK128 enhances the antiviral activity of Maraviroc, and it has favorable, non-antagonist drug interactions with the other existing ART classes.

Example 6: INK128 Inhibits HIV Replication in Humanized Mice

Figure 7A:
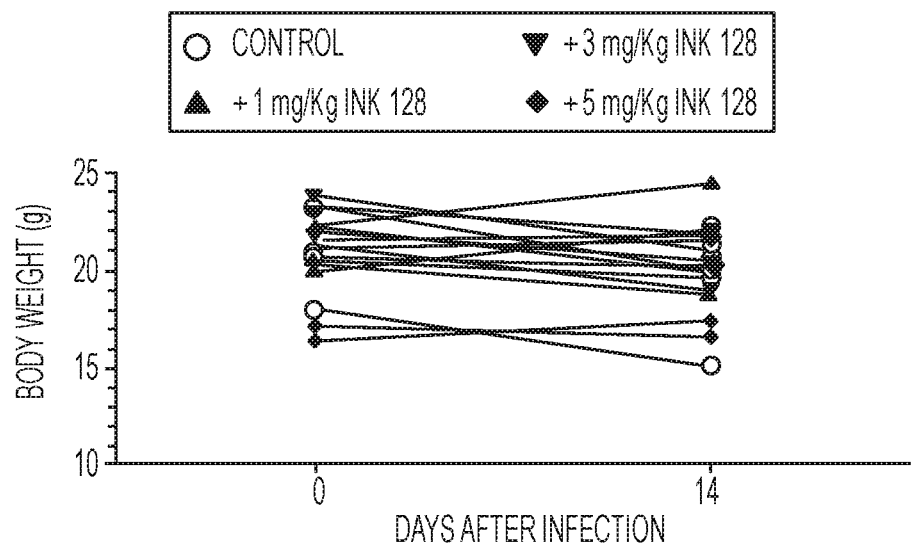
FIG. 7A-7B are graphs showing how INK128 treatment does not result in weight loss in humanized mice.
Figure 7B:
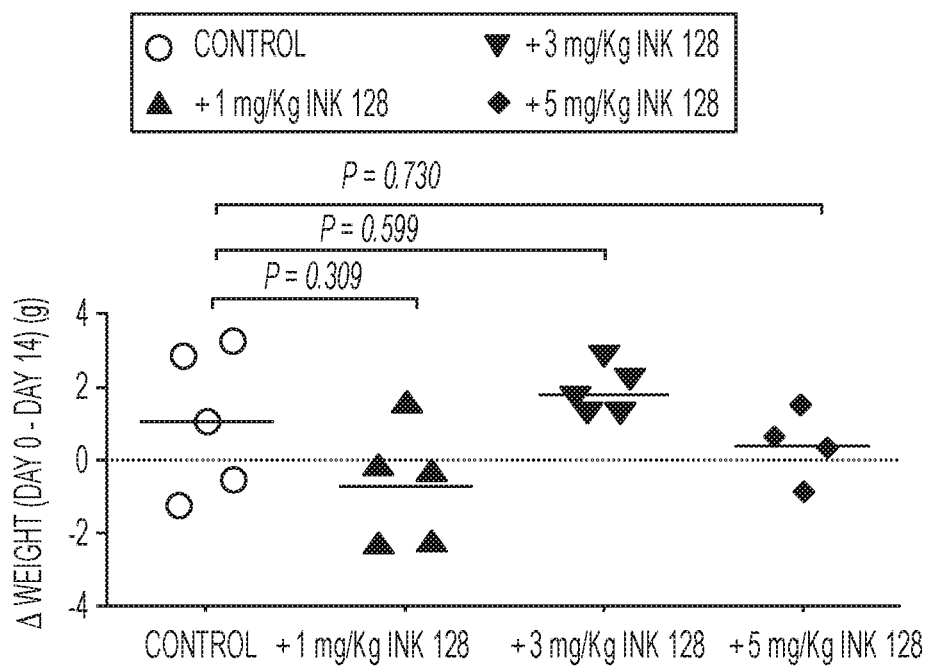
Figure 8A:
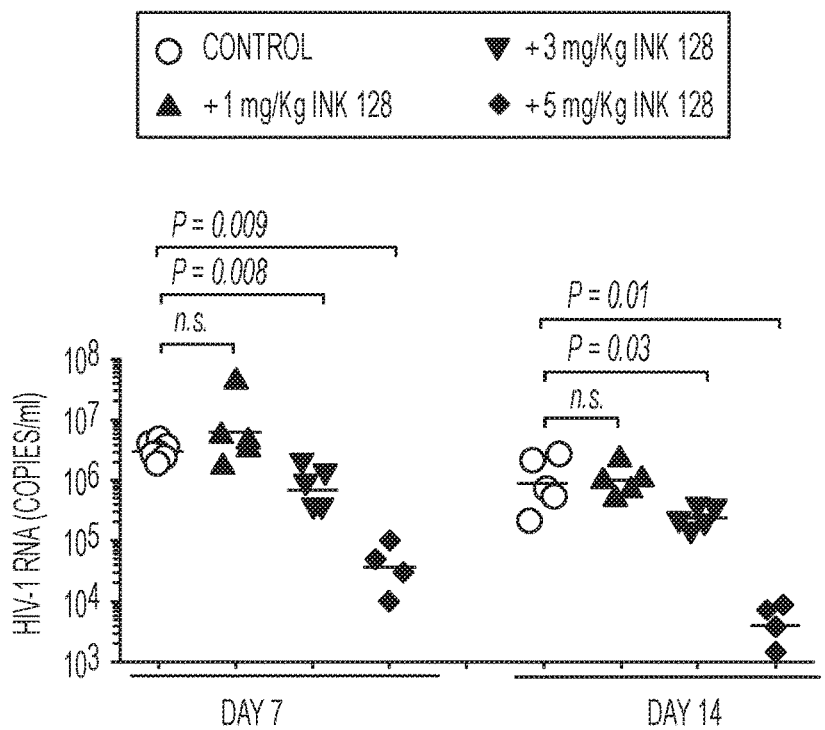
FIG. 8A-8B are graphs that illustrate INK128's reduction of plasma HIV RNA in humanized mice. Five- to seven-week-old NSG mice were intraperitoneally (i.p.) injected with PBLs ($10^7$ per mouse) from healthy donors. Three weeks later, successfully engrafted mice were i.p. injected with 15,000 TCID50s of HIV BaL Immediately after virus challenge, i.p. treatment with INK128 or PBS was initiated and continued daily for 14 days. Plasma HIV RNA (copies per mL) was measured by quantitative RT PCR on days 7 and 14 (FIG. 8A). CD4/CD8 cell ratios on days 7 and 14 retro orbital blood samples were determined by Flow Cytometry Analysis (FIG. 8B) according to an embodiment.
Figure 8B:
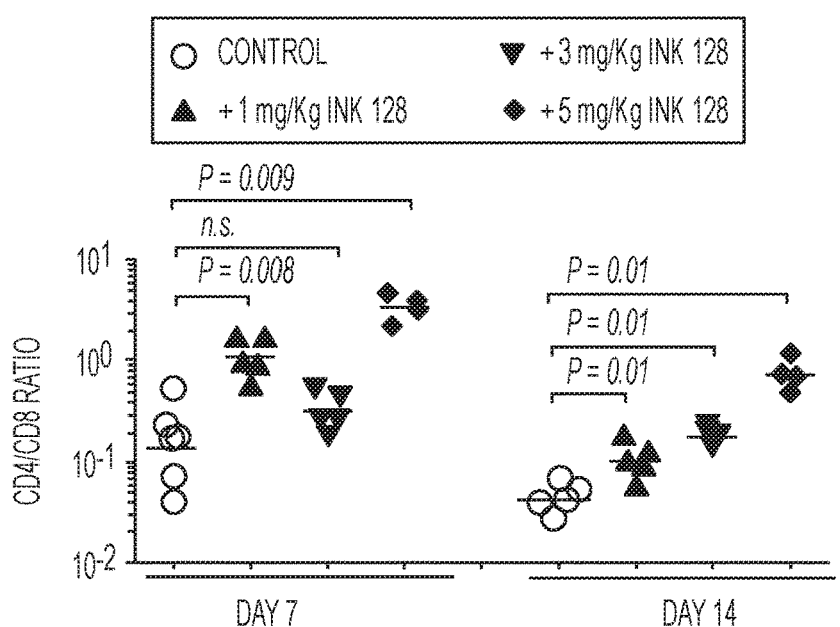

Anti-HIV activity of INK128 was evaluated in vivo, using NOD/SCID/IL-2Rynull (NSG) mice reconstituted with human PBLs and infected with HIV BaL. In pilot experiments, in which uninfected huPBLNSG mice were treated with daily i.p. injections of INK128 at 0.5, 1, 3, 5, and 7 mg/kg for 2 wk, the 7 mg/kg dose was associated with wasting and death. Thus, the antiviral activity of INK128 was evaluated at 0 (PBS) (n=6 mice), 1 mg/kg (n=5), 3 mg/kg (n=5), and 5 mg/kg (n=5). Treatment was initiated immediately after virus injection and continued once daily for 14 days. Treatment had no adverse effects on the weight of the animals compared with controls (FIG. 6A-6B). Two mice, one in the control group and one in the 5 mg INK128/kg group, died in the course of the experiment. We could not determine the cause of death in the two animals, but incidental death, often the result of graft-versus-host disease from the transplanted human cells, is frequent in this animal model (37). On day 7 after infection, control mice (n=6) had mean plasma HIV RNA (copies per mL) of $3.3 \times 10^6$ (range, $2.1 \times 10^6$ to $5.2 \times 10^6$)(FIG. 7A). In INK128-treated mice, mean HIV RNA (copies/mL) were $1.2 \times 107$ (range, $1.7 \times 106$ to $4.5 \times 107$; n=5; P=0.3), $8.5 \times 105$ (range, $3.5 \times 105$ to $1.7 \times 106$; n=5; P=0.008) and $3.8 \times 104$ (range, $1 \times 104$ to $1 \times 105$; n=4; P=0.009), at 1, 3, and 5 mg/kg/day doses, respectively. On day 14 after infection, mean plasma HIV RNA values were $1.2 \times 106$ (range, $2.4 \times 105$ to $2.4 \times 106$) in controls; and $1.1 \times 106$ (range, $5.2 \times 105$ to $2.1 \times 106$; P=0.9), $2.5 \times 105$ (range, $1.4 \times 105$ to $3.8 \times 105$; P=0.03) and $5 \times 103$ (range, $1.3 \times 103$ to $8 \times 103$; P=0.01), at 1, 3, and 5 mg/kg/day doses, respectively. Consistent with reductions in viremia, infected mice treated with INK128 had higher CD4/CD8 ratios than did controls (FIG. 7B). Although CD4/CD8 ratios on day 7 were somewhat variable, day 14 ratios were significantly higher that controls. Day 14 mean CD4/CD8 cell ratios were 0.04 (range, 0.03-0.06) in control mice and 0.11 (range, 0.06-0.18; P=0.01), 0.18 (range, 0.14-0.24; P=0.01), and 0.76 (range, 0.5-1.14; P=0.01), at 1, 3, and 5 mg/kg/day doses, respectively. Together, these data demonstrate that INK128 suppresses viremia of the HIV reference strain BaL in a preclinical animal model. INK128 reduced plasma viremia by more than 2 log 10 units, a decrease in viral load comparable to that achieved with EFdA, a potent NRTI in clinical trials, in a similar experimental setting (38).

Example 7. Torin-2 Inhibits HIV

Figure 9A:
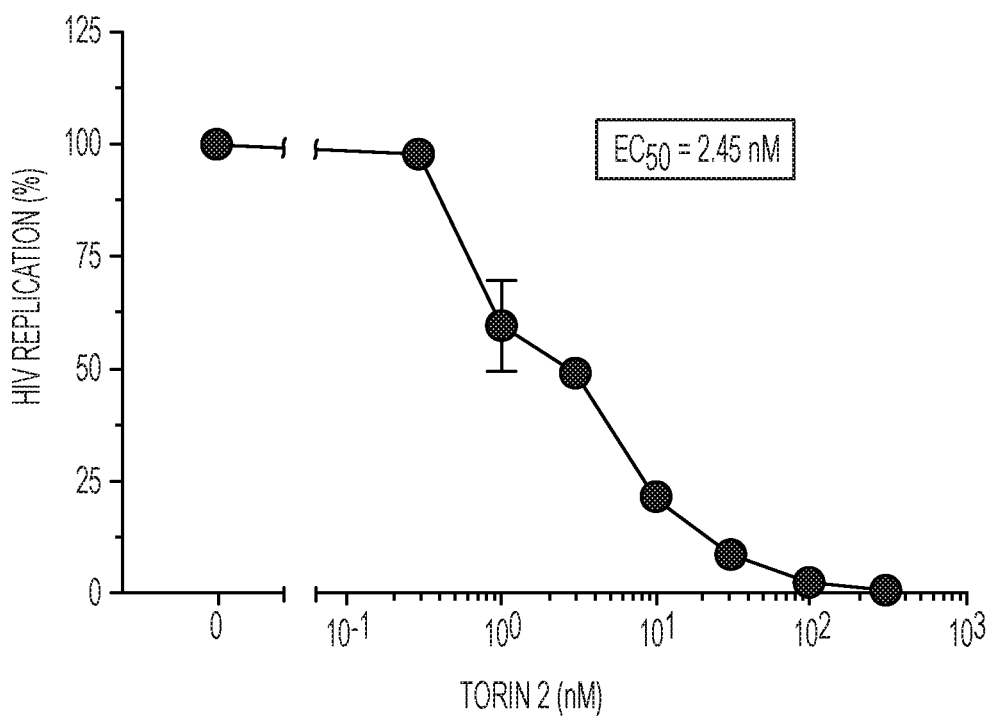
FIG. 9A-9B are graphs showing how Torin-2 inhibits HIV. PHA activated PBMCs were infected with HIV-1 for 2 hours. Infected cells were washed to remove non-adsorbed virus, and plated in culture medium containing IL-2 and various dilutions of Torin-2. Cultures were evaluated for HIV production by measuring HIV p24 levels in the culture supernatants by ELISA (FIG. 9A). Also on day 7, cell viability was measured by MTT assays (FIG. 9B) according to an embodiment.
Figure 9B:
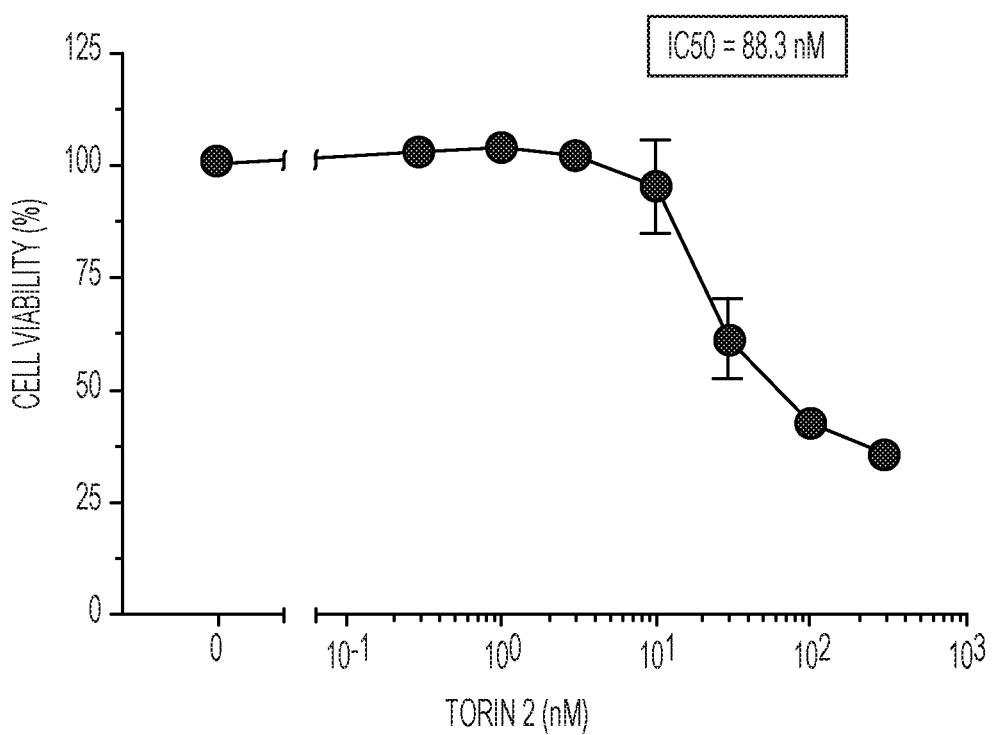

PHA activated PBMCs were infected with HIV-1 for 2 hours. Infected cells were washed to remove non-adsorbed virus, and plated in culture medium containing IL-2 and various dilutions of Torin-2. On day 3, fresh medium with fresh drug was added to the cultures. On day 7, cultures were evaluated for HIV production by measuring HIV p24 levels in the culture supernatants by ELISA (FIG. 9A). Also on day 7, cell viability was measured by MTT assays (FIG. 9B)/

Example 8. INK-128 Inhibits Tumor Growth in NSG Mice

Figure 10A:
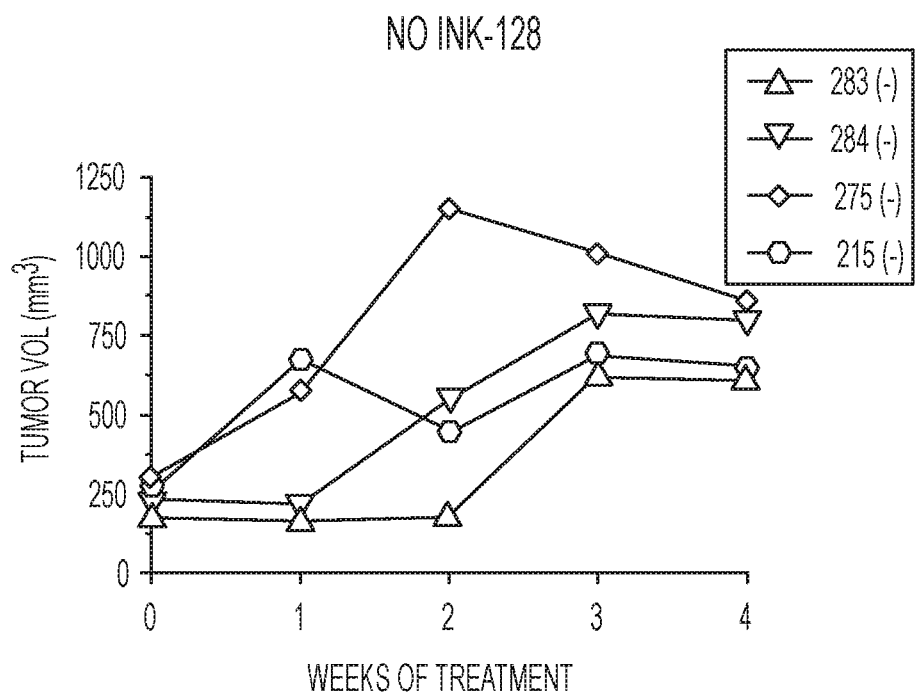
FIG. 10A-10C are graphs illustrating how INK-128 inhibits tumor growth in NSG mice. A xenograft tumor was induced by subcutaneous injection of $5 \times 10^6$ non small cell lung cancer (NSCLC) A549 cells in mice according to an embodiment.
Figure 10B:
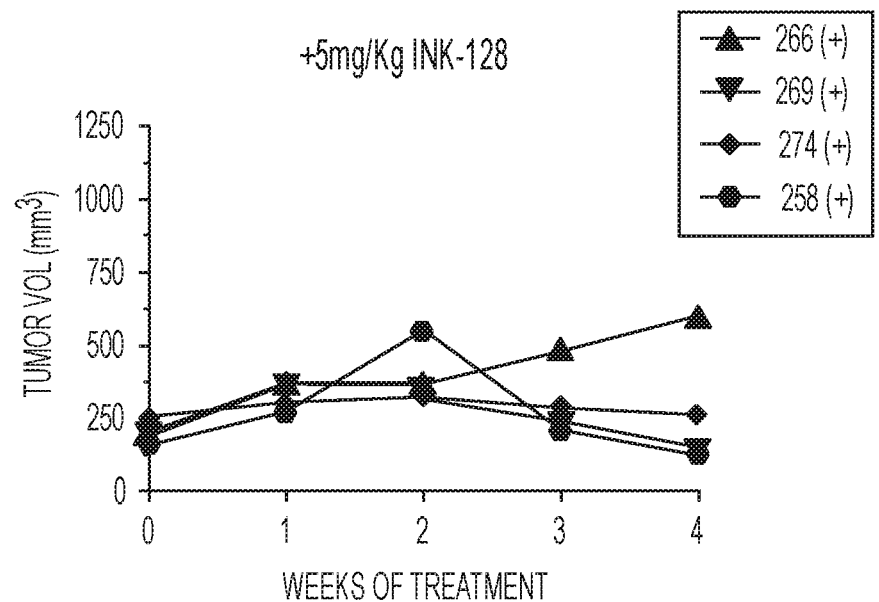
Figure 10C:
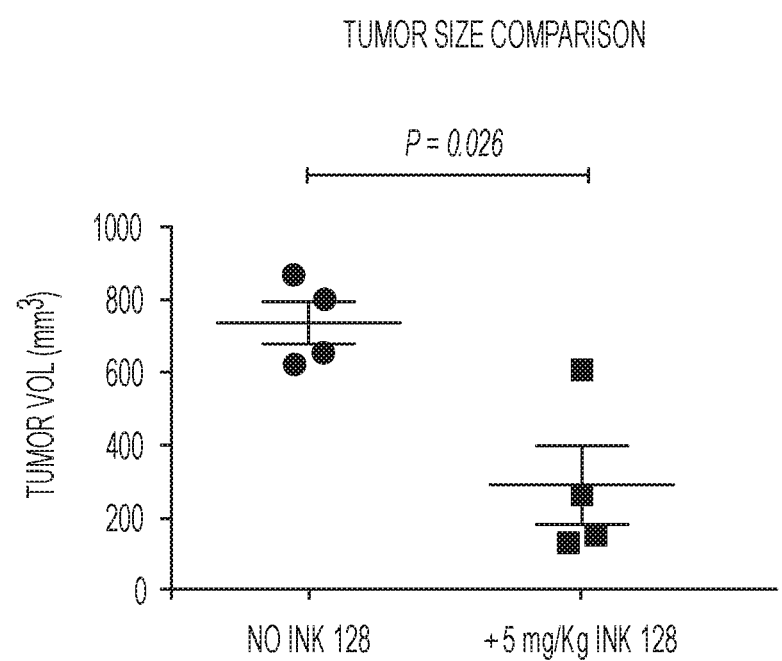

A xenograft tumor was induced by subcutaneous injection of $5 \times 10^6$ non small cell lung cancer (NSCLC) A549 cells in mice. After 3 weeks, tumors became visible (~200 mm$^3$, as measured with calipers). Mice were treated with INK128, or vehicle control (FIG. 10A), daily (via ip) for 4 weeks. INK-128 was used at 5 mg/kg (FIG. 10B). Tumor volume was measured at the indicated time points (FIG. 10C).

REFERENCES

1. Günthard H F, et al.; International Antiviral Society-USA Panel (2014) Antiretroviral treatment of adult HIV infection: 2014 recommendations of the International Antiviral Society-USA Panel. *JAMA* 312(4):410-425.
2. Wong A (2014) The HIV pipeline. *Nat Rev Drug Discov* 13(9):649-650.
3. Pennings P S (2013) HIV Drug Resistance: Problems and Perspectives. *Infect Dis Rep* 5 (Suppl 1):e5.
4. De Clercq E (2013) The nucleoside reverse transcriptase inhibitors, nonnucleoside reverse transcriptase inhibitors, and protease inhibitors in the treatment of HIV infections (AIDS). *Adv Pharmacol* 67:317-358.
5. Dorr P, et al. (2005) Maraviroc (UK-427,857), a potent, orally bioavailable, and selective small-molecule inhibitor of chemokine receptor CCR5 with broad-spectrum anti-human immunodeficiency virus type 1 activity. *Antimicrob Agents Chemother* 49(11):4721-4732.
6. Dilby J M, et al. (1998) Potent suppression of HIV-1 replication in humans by T-20, a peptide inhibitor of gp41-mediated virus entry. *Nat Med* 4(11):1302-1307.
7. Fätkenheuer G, et al. (2005) Efficacy of short-term monotherapy with maraviroc, a new CCR5 antagonist, in patients infected with HIV-1. *Nat Med* 11(11):1170-1172.
8. Kilby J M, et al. (2002) The safety, plasma pharmacokinetics, and antiviral activity of subcutaneous enfuvirtide (T-20), a peptide inhibitor of gp41-mediated virus fusion, in HIV-infected adults. *AIDS Res Hum Retroviruses* 18(10):685-693.
9. Chi H (2012) Regulation and function of mTOR signalling in T cell fate decisions. *Nat Rev Immunol* 12(5):325-338.
10. Zoncu R, Efeyan A, Sabatini D M (2011) mTOR: From growth signal integration to cancer, diabetes and ageing. *Nat Rev Mol Cell Biol* 12(1):21-35.
11. Heredia A, et al. (2008) Reduction of CCR5 with low-dose rapamycin enhances the antiviral activity of vicriviroc against both sensitive and drug-resistant HIV-1. *Proc Natl Acad Sci USA* 105(51):20476-20481.
12. Roy J, Paquette J S, Fortin J F, Tremblay M J (2002) The immunosuppressant rapamycin represses human immunodeficiency virus type 1 replication. *Antimicrob Agents Chemother* 46(11):3447-3455.
13. Heredia A, et al. (2003) Rapamycin causes down-regulation of CCR5 and accumulation of anti-HIV beta-chemokines: An approach to suppress R5 strains of HIV-1. *Proc Natl Acad Sci USA* 100(18):10411-10416.
14. Rai P, et al. (2013) Rapamycin-induced modulation of HIV gene transcription attenuates progression of HIVAN. *Exp Mol Pathol* 94(1):255-261.
15. Heredia A, et al. (2007) Rapamycin reduces CCR5 density levels on CD4 T cells and this effect results in potentiation of Enfuvirtide (T-20) against R5 HIV-1 in vitro. *Anti-microb Agents Chemother* 51(7):2482-2496.
16. Garcia-Martinez J M, et al. (2009) Ku-0063794 is a specific inhibitor of the mammalian target of rapamycin (mTOR). *Biochem J* 421(1):29-42.
17. Thoreen C C, et al. (2009) An ATP-competitive mammalian target of rapamycin inhibitor reveals rapamycin-resistant functions of mTORC1. *J Biol Chem* 284(12): 8023-8032.
18. Yu K, et al. (2009) Biochemical, cellular, and in vivo activity of novel ATP-competitive and selective inhibitors of the mammalian target of rapamycin. *Cancer Res* 69(15): 6232-6240.
19. Feldman M E, et al. (2009) Active-site inhibitors of mTOR target rapamycin-resistant outputs of mTORC1 and mTORC2. *PLoS Biol* 7(2):e38.
20. Moschetta M, Reale A, Marasco C, Vacca A, Carrath M R (2014) Therapeutic targeting of the mTOR-signalling pathway in cancer: Benefits and limitations. *Br J Pharmacol* 171(16):3801-3813.
21. Facchinetti V, et al. (2008) The mammalian target of rapamycin complex 2 controls folding and stability of Akt and protein kinase C. *EMBO J* 27(14):1932-1943.

22. Ikenoue T, Inoki K, Yang Q, Zhou X, Guan K L (2008) Essential function of TORC2 in PKC and Akt turn motif phosphorylation, maturation and signalling. *EMBO J* 27(14): 1919-1931.
23. Chan J K, Greene W C (2012) Dynamic roles for NF-κB in HTLV-I and HIV-1 retroviral pathogenesis. *Immunol Rev* 246(1):286-310.
24. Nabel G, Baltimore D (1987) An inducible transcription factor activates expression of human immunodeficiency virus in T cells. *Nature* 326(6114):711-713.
25. Hsieh A C, et al. (2012) The translational landscape of mTOR signalling steers cancer initiation and metastasis. *Nature* 485(7396):55-61.
26. INK128 in models of B-cell acute lymphoblastic leukemia. Leukemia 27(3):586-594.
27. Slotkin E K, et al. (2015) MLN0128, an ATP-competitive mTOR kinase inhibitor with potent in vitro and in vivo antitumor activity, as potential therapy for bone and soft-tissue sarcoma. *Mol Cancer Ther* 14(2):395-406.
28. Johnston E, et al. (2005) Panel of prototypical infectious molecular HIV-1 clones containing multiple nucleoside reverse transcriptase inhibitor resistance mutations. *AIDS* 19(7):731-733.
29. Platt E J, Wehrly K, Kuhmann S E, Chesebro B, Kabat D (1998) Effects of CCR5 and CD4 cell surface concentrations on infections by macrophagetropic isolates of human immunodeficiency virus type 1. *J Virol* 72(4): 2855-2864.
30. Reeves J D, et al. (2002) Sensitivity of HIV-1 to entry inhibitors correlates with envelope/coreceptor affinity, receptor density, and fusion kinetics. *Proc Natl Acad Sci USA* 99(25): 16249-16254.
31. Reynes J, et al. (2001) CD4 T cell surface CCR5 density as a host factor in HIV-1 disease progression. *AIDS* 15(13):1627-1634.
32. Reynes J, et al. (2000) CD4+ T cell surface CCR5 density as a determining factor of virus load in persons infected with human immunodeficiency virus type 1. *J Infect Dis* 181(3):927-932.
33. Folks T M, Justement J, Kinter A, Dinarello C A, Fauci A S (1987) Cytokine-induced expression of HIV-1 in a chronically infected promonocyte cell line. *Science* 238 (4828): 800-802.
34. Michael N L, et al. (1991) Induction of human immunodeficiency virus type 1 expression in chronically infected cells is associated primarily with a shift in RNA splicing patterns. *J Virol* 65 (12):7084.
35. Pomerantz R J, Trono D, Feinberg M B, Baltimore D (1990) Cells nonproductively infected with HIV-1 exhibit an aberrant pattern of viral RNA expression: A molecular model for latency. *Cell* 61(7):1271-1276.
36. Altman J K, et al. (2011) Dual mTORC2/mTORC1 targeting results in potent suppressive effects on acute myeloid leukemia (AML) progenitors. *Clin Cancer Res* 17(13): 4378-4388.
37. Akkina R (2013) New generation humanized mice for virus research: Comparative aspects and future prospects. *Virology* 435(1):14-28.
38. Hattori S, et al. (2009) Potent activity of a nucleoside reverse transcriptase inhibitor, 4'-ethynyl-2-fluoro-2'-deoxyadenosine, against human immunodeficiency virus type 1 infection in a model using human peripheral blood mononuclear cell-transplanted NOD/SCID Janus kinase 3 knockout mice. *Antimicrob Agents Chemother* 53(9): 3887-3893.
39. Deeks S G, Lewin S R, Havlir D V (2013) The end of AIDS: HIV infection as a chronic disease. *Lancet* 382 (9903):1525-1533.
40. Gilliam B L, et al. (2007) Rapamycin reduces CCR5 mRNA levels in macaques: Potential applications in HIV-1 prevention and treatment. *AIDS* 21(15):2108-2110.
41. Nicoletti F, et al. (2009) Inhibition of human immunodeficiency virus (HIV-1) infection in human peripheral blood leucocytes-SCID reconstituted mice by rapamycin. *Clin Exp Immunol* 155(1):28-34.
42. Stock P G, et al.; for Solid Organ Transplantation in HIV Study Investigators (2014) Reduction of HIV persistence following transplantation in HIV-infected kidney transplant recipients. *Am J Transplant* 14(5): 1136-1141.
43. Fiume G, et al. (2012) Human immunodeficiency virus-1 Tat activates NF-κB physical interaction with IκB-α and p65. *Nucleic Acids Res* 40(8):3548-3562.
44. Barboric M, Nissen R M, Kanazawa S, Jabrane-Ferrat N, Peterlin B M (2001) N F-kappaB binds P-TEFb to stimulate transcriptional elongation by RNA polymerase II. *Mol Cell* 8(2):327-337.
45. Janes M R, et al. (2010) Effective and selective targeting of leukemia cells using a TORC1/2 kinase inhibitor. *Nat Med* 16(2):205-213.
46. Wei P, Garber M E, Fang S M, Fischer W H, Jones K A (1998) A novel CDK9-associated C-type cyclin interacts directly with HIV-1 Tat and mediates its high-affinity, loop-specific binding to TAR RNA. *Cell* 92(4):451-462.
47. He N, et al. (2010) HIV-1 Tat and host AFF4 recruit two transcription elongation factors into a bifunctional complex for coordinated activation of HIV-1 transcription. *Mol Cell* 38(3):428-438.
48. Sobhian B, et al. (2010) HIV-1 Tat assembles a multifunctional transcription elongation complex and stably associates with the 7SK snRNP. *Mol Cell* 38(3):439-451.
49. Simioni C, et al. (2014) Activity of the novel mTOR inhibitor Torin-2 in B-precursor acute lymphoblastic leukemia and its therapeutic potential to prevent Akt reactivation. *Oncotarget* 5(20):10034-10047.
50. Takeuchi C S, et al. (2013) Discovery of a novel class of highly potent, selective, ATP-competitive, and orally bioavailable inhibitors of the mammalian target of rapamycin (mTOR). *J Med Chem* 56(6):2218-2234.
51. Venkatesha V A, et al. (2014) P7170, a novel inhibitor of mTORC1/mTORC2 and Activin receptor-like Kinase 1 (ALK1) inhibits the growth of non small cell lung cancer. *Mol Cancer* 13:259.
52. Gravina G L, et al. (2014) Torc1/Torc2 inhibitor, Palomid 529, enhances radiation response modulating CRM1-mediated survivin function and delaying DNA repair in prostate cancer models. *Prostate* 74(8):852-868.
53. Lin F, Buil L, Sherris D, Beijnen J H, van Tellingen O (2013) Dual mTORC1 and mTORC2 inhibitor Palomid 529 penetrates the blood-brain barrier without restriction by ABCB1 and ABCG2. *Int J Cancer* 133(5):1222-1233.
54. Liao H, et al. (2015) Dramatic antitumor effects of the dual mTORC1 and mTORC2 inhibitor AZD2014 in hepatocellular carcinoma. *Am J Cancer Res* 5(1):125-139.
55. Araki K, et al. (2009) mTOR regulates memory CD8 T-cell differentiation. *Nature* 460(7251):108-112.
56. Pearce E L, et al. (2009) Enhancing CD8 T-cell memory by modulating fatty acid metabolism. *Nature* 460(7251): 103-107.

57. Haidinger M, et al. (2010) A versatile role of mammalian target of rapamycin in human dendritic cell function and differentiation. *J Immunol* 185(7):3919-3931.
58. Deeks S G, Phillips A N (2009) HIV infection, antiretroviral treatment, ageing, and non AIDS related morbidity. *BMJ* 338:a3172.
59. Salkowitz J R, et al. (2003) CCR5 promoter polymorphism determines macrophage CCR5 density and magnitude of HIV-1 propagation in vitro. *Clin Immunol* 108(3): 234-240.
60. Lin Y L, et al. (2002) Cell surface CCR5 density determines the post entry efficiency of R5 HIV-1 infection. *Proc Natl Acad Sci USA* 99(24):15590-15595.
61. Butler S L, Hansen M S, Bushman F D (2001) A quantitative assay for HIV DNA integration in vivo. *Nat Med* 7(5):631-634.
62. König R, et al. (2008) Global analysis of host-pathogen interactions that regulate early-stage HIV-1 replication. *Cell* 135(1):49-60.Hermankova M, et al. (2003) Analysis of human immunodeficiency virus type 1 gene expression in latently infected resting CD4+ T lymphocytes in vivo. *J Virol* 77(13): 7383-7392.
63. Ou C Y, et al. (1988) DNA amplification for direct detection of HIV-1 in DNA of peripheral blood mononuclear cells. *Science* 239(4837):295-297.

What is claimed is:

1. A method of enhancing the antiviral potency of the CCR5 antagonist therapeutic agent maravirac, comprising administering maraviroc in combination with INK128, wherein the INK128 enhances the antiviral potency of the maraviroc in a synergistic manner.

2. The method of enhancing the antiviral potency of the CCR5 antagonist therapeutic agent maravirac according to claim 1, wherein the INK128 is administered in an amount to achieve a 200 nM plasma concentration in the patient.

3. The method of enhancing the antiviral potency of the CCR5 antagonist therapeutic agent maravirac according to claim 1, wherein the INK128 is administered in a dose of about 0.5 mg to about 4 mg.

4. The method of enhancing the antiviral potency of the CCR5 antagonist therapeutic agent maravirac according to claim 1, wherein the INK128 is administered in a dose of about 0.5 mg/kg.

* * * * *

```
SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
gctctctggc taactaggga ac                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
tgactaaaag ggtctgaggg at                                              22

<210> SEQ ID NO 3
<211> LENGTH: 25
<212> TYPE: DNA
<213> ORGANISM: Artificial Sequence
<220> FEATURE:
<223> OTHER INFORMATION: Synthetic primer: Alu

<400> SEQUENCE: 3
gcctcccaaa gtgctgggat tacag                                           25

<210> SEQ ID NO 4
<211> LENGTH: 22
<212> TYPE: DNA
<213> ORGANISM: Artificial Sequence
<220> FEATURE:
<223> OTHER INFORMATION: Synthetic primer: Gag

<400> SEQUENCE: 4
gctctcgcac ccatctctct cc                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic primer: LTR-R

<400> SEQUENCE: 5
gcctcaataa agcttgcctt ga                                              22
```

```
<210> SEQ ID NO 6
<211> LENGTH: 24
<212> TYPE: DNA
<213> ORGANISM: Artificial Sequence
<220> FEATURE:
<223> OTHER INFORMATION: Synthetic primer: LTR-U5

<400> SEQUENCE: 6
tccacactga ctaaagggt ctga                                          24
```